US012616526B2

(12) United States Patent
Hendricks et al.

(10) Patent No.: US 12,616,526 B2
(45) Date of Patent: May 5, 2026

(54) SYSTEMS AND METHODS FOR OPERATIVE MICROSCOPE TRACKING FOR TECHNICAL GUIDANCE

(71) Applicant: Dignity Health, San Francisco, CA (US)

(72) Inventors: Benjamin Hendricks, San Francisco, CA (US); Michael Lawton, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 453 days.

(21) Appl. No.: 18/028,649

(22) PCT Filed: Sep. 28, 2021

(86) PCT No.: PCT/US2021/052371
§ 371 (c)(1),
(2) Date: Mar. 27, 2023

(87) PCT Pub. No.: WO2022/067241
PCT Pub. Date: Mar. 31, 2022

(65) Prior Publication Data
US 2023/0363829 A1       Nov. 16, 2023

Related U.S. Application Data

(60) Provisional application No. 63/147,395, filed on Feb. 9, 2021, provisional application No. 63/141,122, filed
(Continued)

(51) Int. Cl.
*A61B 34/00* (2016.01)
*A61B 34/20* (2016.01)
(Continued)

(52) U.S. Cl.
CPC .............. *A61B 34/20* (2016.02); *A61B 90/20* (2016.02); *A61B 90/37* (2016.02); *G16H 30/40* (2018.01); *A61B 2034/256* (2016.02)

(58) Field of Classification Search
None
See application file for complete search history.

(56) References Cited

U.S. PATENT DOCUMENTS

| 8,116,848 | B2 * | 2/2012 | Shahidi | ................. | A61B 90/36 |
| | | | | | 600/407 |
| 2016/0278678 | A1 | 9/2016 | Valdes et al. | | |

(Continued)

OTHER PUBLICATIONS

Patent Cooperation Treaty, International Search Report and Written Opinion, International Application No. PCT/US2021/052371, date of mailing Dec. 28, 2021, 12 pages.
(Continued)

*Primary Examiner* — Yi Wang
(74) *Attorney, Agent, or Firm* — Polsinelli PC

(57) ABSTRACT

A system provides a computer-implemented rendered visualization of a surgeon's path or "roadmap" to a particular target region during a surgical case are disclosed herein. The system includes an approach library in communication with an operating microscope that includes data related to various surgical approach sequences, or "roadmaps" to various target regions. The approach library can be populated by the system and analyzed for variance and trends, as well as provide direct or indirect instruction and guidance through a display member during a surgical case.

20 Claims, 22 Drawing Sheets

Related U.S. Application Data on Jan. 25, 2021, provisional application No. 63/084,070, filed on Sep. 28, 2020.

(51) Int. Cl.
  A61B 90/00     (2016.01)
  A61B 90/20     (2016.01)
  G16H 30/40     (2018.01)

(56)            References Cited

U.S. PATENT DOCUMENTS

| | | |
|---|---|---|
| 2019/0015162 A1 | 1/2019 | Abhari et al. |
| 2019/0206562 A1 | 7/2019 | Shelton, IV et al. |
| 2019/0269476 A1 | 9/2019 | Bowling et al. |
| 2019/0307362 A1 | 10/2019 | Piron et al. |

OTHER PUBLICATIONS

European Patent Office, Extended European Search Report, Application No. 21873633.8, Sep. 17, 2024, 10 pages.

\* cited by examiner

10

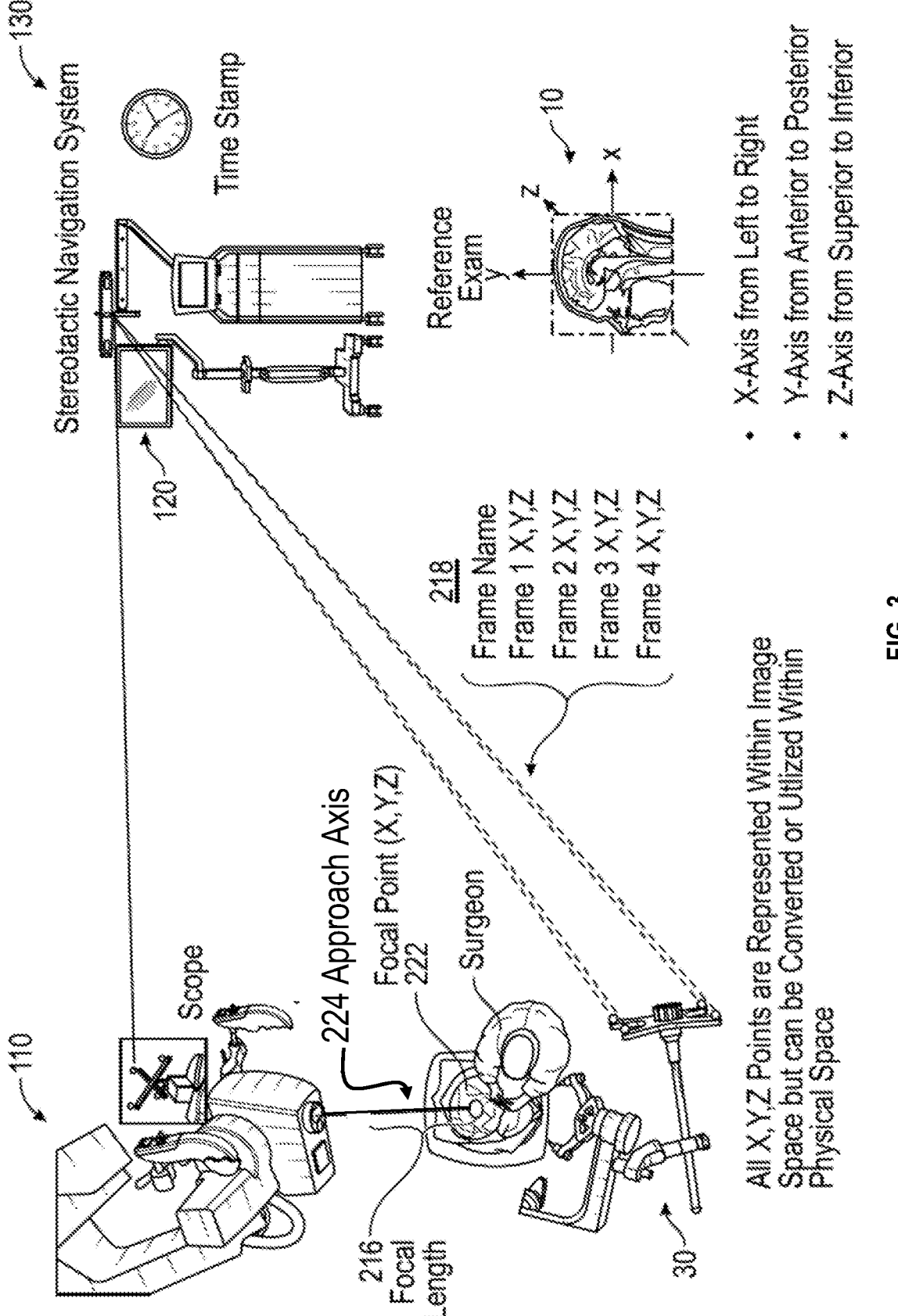

130 Stereotactic Navigation System

Time Stamp

120

10
Reference Exam

- X-Axis from Left to Right
- Y-Axis from Anterior to Posterior
- Z-Axis from Superior to Inferior 218
Frame Name
Frame 1 X,Y,Z
Frame 2 X,Y,Z
Frame 3 X,Y,Z
Frame 4 X,Y,Z

110

Scope

224 Approach Axis
Focal Point (X,Y,Z)
222

Surgeon

216 Focal Length

30

All X,Y,Z Points are Represented Within Image Space but can be Converted or Utilized Within Physical Space

FIG. 3

FIELD OF VIEW = FIELD NUMBER (FN) ÷ OBJECTIVE MAGNIFICATION

FIELD OF VIEW 126

Zoom Adjustment

APPROACH LIBRARY 300

340

| ServerTime | ReferenceExamIDs | ScopeName | tipX | tipY | tipZ | hindX | hindY | hindZ | Focal Length |
|---|---|---|---|---|---|---|---|---|---|
| A | B | C | D | E | F | G | H | I | J |
| 22:54:35.987618 | [CT-1][4]WAND | ZEISS_KINEVO 181010-313 | 142.958 | 12.763 | -1948.76 | -334.009 | 111.674 | -1881.74 | 491.704 |
| 22:54:36.496782 | [CT-1][4]WAND | ZEISS_KINEVO 181010-313 | 142.956 | 12.787 | -1948.76 | -334.003 | 111.718 | -1881.72 | 491.704 |
| 22:54:37.009848 | [CT-1][4]WAND | ZEISS_KINEVO 181010-313 | 142.969 | 12.8011 | -1948.75 | -333.99 | 111.743 | -1881.72 | 491.704 |
| 22:54:37.525750 | [CT-1][4]WAND | ZEISS_KINEVO 181010-313 | 142.949 | 12.7467 | -1948.79 | -334.012 | 111.716 | -1881.74 | 491.704 |
| 22:54:38.033698 | [CT-1][4]WAND | ZEISS_KINEVO 181010-313 | 142.944 | 12.7955 | -1948.8 | -334.014 | 111.717 | -1881.73 | 491.704 |
| 22:54:38.535032 | [CT-1][4]WAND | ZEISS_KINEVO 181010-313 | 142.958 | 12.7674 | -1948.77 | -334.017 | 111.649 | -1881.77 | 491.704 |
| 22:54:39.035011 | [CT-1][4]WAND | ZEISS_KINEVO 181010-313 | 142.951 | 12.7832 | -1948.78 | -334.018 | 111.676 | -1881.75 | 491.704 |
| 22:54:39.534687 | [CT-1][4]WAND | ZEISS_KINEVO 181010-313 | 142.975 | 12.7713 | -1948.75 | -334.003 | 111.655 | -1881.77 | 491.704 |
| 22:54:40.033729 | [CT-1][4]WAND | ZEISS_KINEVO 181010-313 | 142.938 | 12.7775 | -1948.8 | -334.027 | 111.677 | -1881.74 | 491.704 |
| 22:54:40.536831 | [CT-1][4]WAND | ZEISS_KINEVO 181010-313 | 142.936 | 12.7646 | -1948.79 | -334.034 | 111.643 | -1881.75 | 491.704 |
| 22:54:41.044089 | [CT-1][4]WAND | ZEISS_KINEVO 181010-313 | 142.95 | 12.7874 | -1948.76 | -334.016 | 111.687 | -1881.72 | 491.704 |
| 22:54:41.545970 | [CT-1][4]WAND | ZEISS_KINEVO 181010-313 | 142.938 | 12.7839 | -1948.79 | -334.025 | 111.688 | -1881.73 | 491.704 |
| 22:54:42.043992 | [CT-1][4]WAND | ZEISS_KINEVO 181010-313 | 142.95 | 12.7744 | -1948.77 | -334.018 | 111.676 | -1881.74 | 491.704 |
| 22:54:42.543749 | [CT-1][4]WAND | ZEISS_KINEVO 181010-313 | 142.941 | 12.7753 | -1948.77 | -334.026 | 111.67 | -1881.73 | 491.704 |
| 22:54:43.043854 | [CT-1][4]WAND | ZEISS_KINEVO 181010-313 | 142.967 | 12.774 | -1948.74 | -334.005 | 111.676 | -1881.74 | 491.704 |
| 22:54:43.544552 | [CT-1][4]WAND | ZEISS_KINEVO 181010-313 | 142.979 | 12.7627 | -1948.72 | -333.998 | 111.661 | -1881.76 | 491.704 |
| 22:54:44.044837 | [CT-1][4]WAND | ZEISS_KINEVO 181010-313 | 142.957 | 12.7823 | -1948.75 | -334.009 | 111.7 | -1881.73 | 491.704 |
| 22:54:44.545804 | [CT-1][4]WAND | ZEISS_KINEVO 181010-313 | 142.967 | 12.7833 | -1948.74 | -333.997 | 111.714 | -1881.73 | 491.704 |
| 22:54:45.044202 | [CT-1][4]WAND | ZEISS_KINEVO 181010-313 | 142.904 | 12.998 | -1948.92 | -334.045 | 111.893 | -1881.76 | 491.704 |

| A | K | L | M | N | O | P | Q | R | S | T | U | V | W | X | Y |
|---|---|---|---|---|---|---|---|---|---|---|---|---|---|---|---|
| | Depth of Field | Zoom | FrameName | FMIx | FMIy | FMIz | FM2x | FM2y | FM2z | FM3x | FM3y | FM3z | FM4x | FM4y | FM4z |
| 22:54:35.386/5328 | 25.88658 | 391 | Small Passive Cranial Frame | 260.478 | -77.1342 | -1526.53 | 200.475 | 6.03227 | -1601.06 | 193.039 | -153.947 | -1560.9 | 142.357 | -67.7957 | -1627.94 |
| 22:54:36.496782 | 25.88658 | 391 | Small Passive Cranial Frame | 260.466 | -77.1137 | -1526.52 | 200.463 | 6.02161 | -1601.06 | 193.03 | -153.938 | -1560.9 | 142.348 | -67.7984 | -1627.95 |
| 22:54:37.0039848 | 25.88658 | 391 | Small Passive Cranial Frame | 260.461 | -77.1133 | -1526.53 | 200.459 | 6.02162 | -1601.08 | 193.026 | -153.939 | -1560.89 | 142.345 | -67.7917 | -1627.97 |
| 22:54:37.5157907 | 25.88658 | 391 | Small Passive Cranial Frame | 260.466 | -77.1186 | -1526.54 | 200.461 | 6.01823 | -1601.07 | 193.025 | -153.944 | -1560.89 | 142.345 | -67.7935 | -1627.96 |
| 22:54:38.0538388 | 25.88658 | 391 | Small Passive Cranial Frame | 260.469 | -77.1329 | -1526.54 | 200.463 | 6.01505 | -1601.07 | 193.028 | -153.947 | -1560.89 | 142.346 | -67.7982 | -1627.96 |
| 22:54:39.535033 | 25.88658 | 391 | Small Passive Cranial Frame | 260.475 | -77.1292 | -1526.55 | 200.469 | 6.01316 | -1601.07 | 193.032 | -153.949 | -1560.9 | 142.351 | -67.7987 | -1627.94 |
| 22:54:39.035011 | 25.88658 | 391 | Small Passive Cranial Frame | 260.478 | -77.132 | -1526.54 | 200.473 | 6.009869 | -1601.06 | 193.037 | -153.951 | -1560.91 | 142.355 | -67.8015 | -1627.95 |
| 22:54:39.538668 | 25.88658 | 391 | Small Passive Cranial Frame | 260.479 | -77.3338 | -1526.54 | 200.472 | 6.00713 | -1601.05 | 193.037 | -153.954 | -1560.92 | 142.354 | -67.8009 | -1627.94 |
| 22:54:40.536831 | 25.88658 | 391 | Small Passive Cranial Frame | 260.48 | -77.135 | -1526.55 | 200.475 | 6.0045 | -1601.05 | 193.041 | -153.954 | -1560.93 | 142.357 | -67.8011 | -1627.95 |
| 22:54:40.536834 | 25.88658 | 391 | Small Passive Cranial Frame | 260.483 | -77.3375 | -1526.55 | 200.48 | 6.00317 | -1601.06 | 193.04 | -153.956 | -1560.92 | 142.359 | -67.8021 | -1627.95 |
| 22:54:41.0440089 | 25.88658 | 391 | Small Passive Cranial Frame | 260.48 | -77.1396 | -1526.53 | 200.48 | 6.00222 | -1601.06 | 193.038 | -153.956 | -1560.92 | 142.359 | -67.8046 | -1627.94 |
| 22:54:41.5459977 | 25.88658 | 391 | Small Passive Cranial Frame | 260.48 | -77.1419 | -1526.53 | 200.48 | 6.000040 | -1601.05 | 193.039 | -153.958 | -1560.92 | 142.359 | -67.8061 | -1627.94 |
| 22:54:42.0453992 | 25.88658 | 391 | Small Passive Cranial Frame | 260.478 | -77.1404 | -1526.53 | 200.477 | 6.00009 | -1601.06 | 193.037 | -153.96 | -1560.91 | 142.357 | -67.8053 | -1627.94 |
| 22:54:42.5431749 | 25.88658 | 391 | Small Passive Cranial Frame | 260.468 | -77.1164 | -1526.53 | 200.466 | 6.00313 | -1601.06 | 193.035 | -153.957 | -1560.9 | 142.34 | -67.8029 | -1627.94 |
| 22:54:43.5485552 | 25.88658 | 391 | Small Passive Cranial Frame | 260.457 | -77.1122 | -1526.52 | 200.452 | 6.03146 | -1601.06 | 193.022 | -153.943 | -1560.91 | 142.34 | -67.7911 | -1627.94 |
| 22:54:43.5445552 | 25.88658 | 391 | Small Passive Cranial Frame | 260.455 | -77.1122 | -1526.52 | 200.452 | 6.021.46 | -1601.06 | 193.02 | -153.938 | -1560.91 | 142.338 | -67.7866 | -1627.94 |
| 22:54:44.044837 | 25.88658 | 391 | Small Passive Cranial Frame | 260.457 | -77.1127 | -1526.52 | 200.454 | 6.0217S | -1601.06 | 193.022 | -153.939 | -1560.9 | 142.34 | -67.7875 | -1627.94 |
| 22:54:44.545804 | 25.88658 | 391 | Small Passive Cranial Frame | 260.46 | -77.1143 | -1526.52 | 200.456 | 6.0208 | -1601.06 | 193.025 | -153.939 | -1560.9 | 142.344 | -67.7877 | -1627.94 |
| 22:54:45.044202 | 25.88658 | 391 | Small Passive Cranial Frame | 260.468 | -77.1158 | -1526.52 | 200.467 | 6.01976 | -1601.06 | 193.032 | -153.941 | -1560.9 | 142.352 | -67.7879 | -1627.95 |

FIG. 10B

126
122
122  124
DISPLAY MEMBER 120
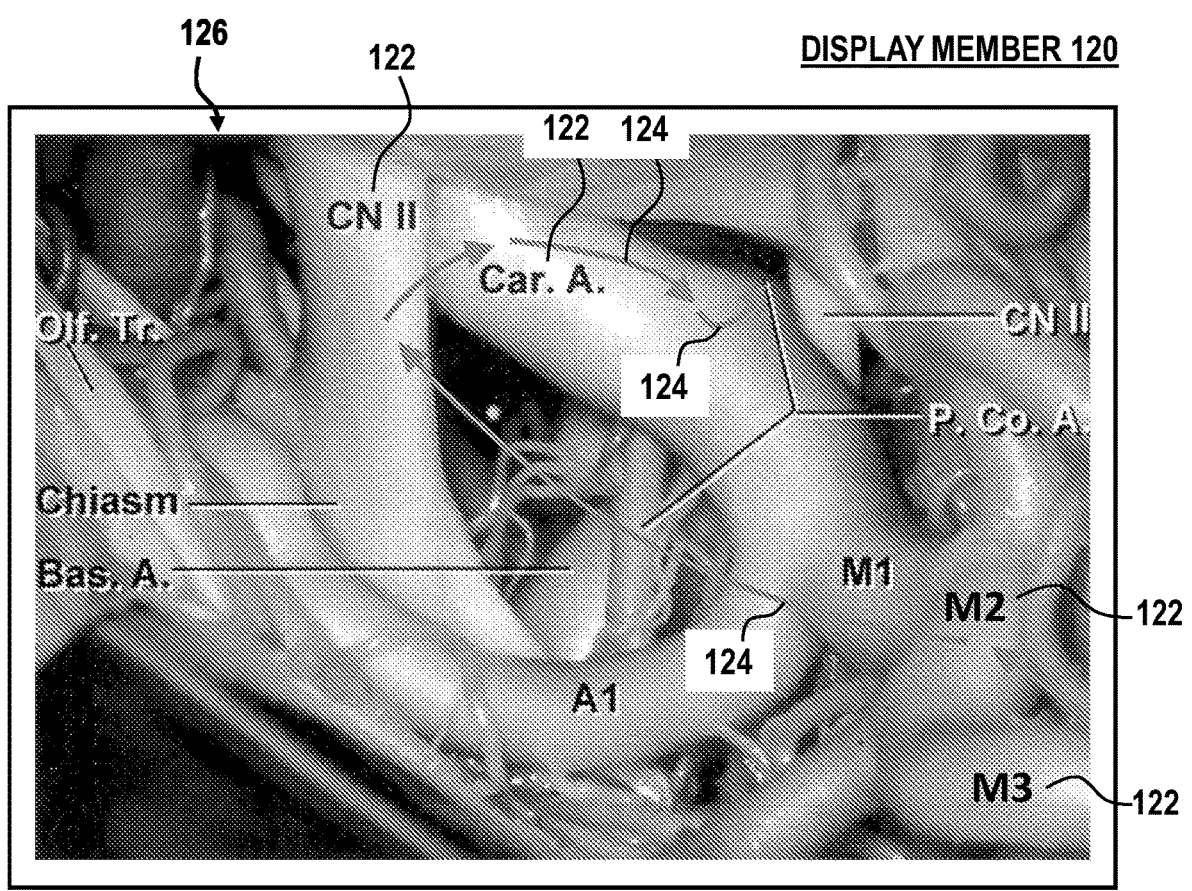
124
124
122
122
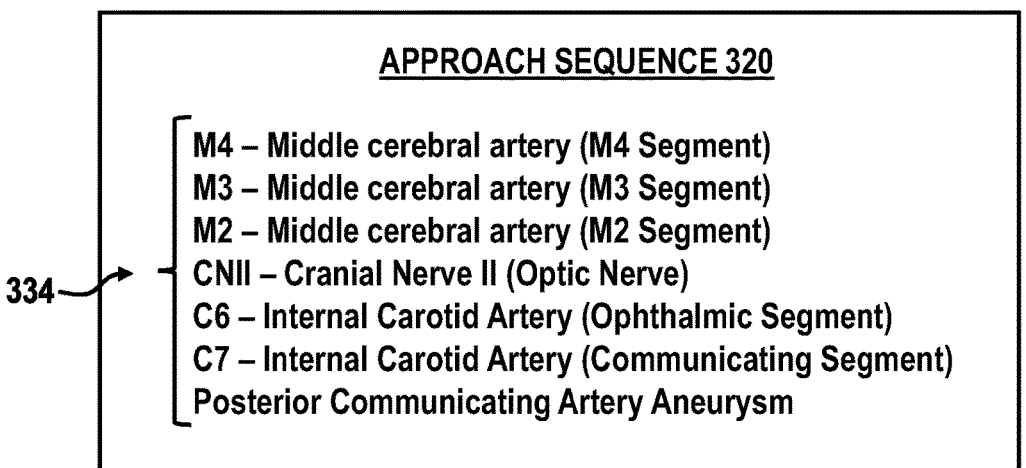
APPROACH SEQUENCE 320
334
M4 – Middle cerebral artery (M4 Segment)
M3 – Middle cerebral artery (M3 Segment)
M2 – Middle cerebral artery (M2 Segment)
CNII – Cranial Nerve II (Optic Nerve)
C6 – Internal Carotid Artery (Ophthalmic Segment)
C7 – Internal Carotid Artery (Communicating Segment)
Posterior Communicating Artery Aneurysm
FIG. 12

400

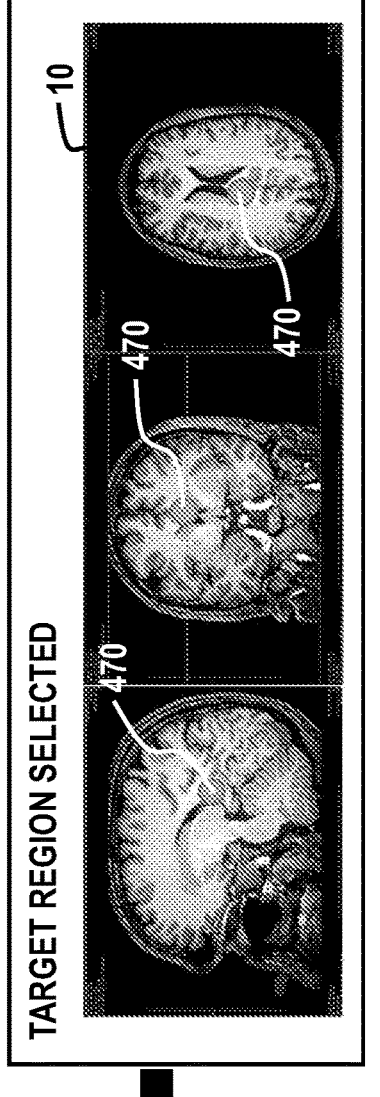

TARGET REGION SELECTED

APPROACH SELECTION
1. POSTERIOR INTERHEMISPHERIC APPROACH
2. SUPRACEREBELLAR TRANSTENTORIAL APPROACH
3. INFRAOCCIPITAL APPROACH
4. SUPERIOR PARIETAL LOBULE APPROACH

USER INTERFACE DISPLAYS GENERIC CARTESIAN MAP

SEQUENTIAL LANDMARK MAP
1. INION
2. TORCULA
3. POSTERIOR CEREBELLAR TENTORIUM
4. ANTERIOR CEREBELLAR TENTORIUM
5. VEIN OF GALEN
6. CORPUS CALLOSUM

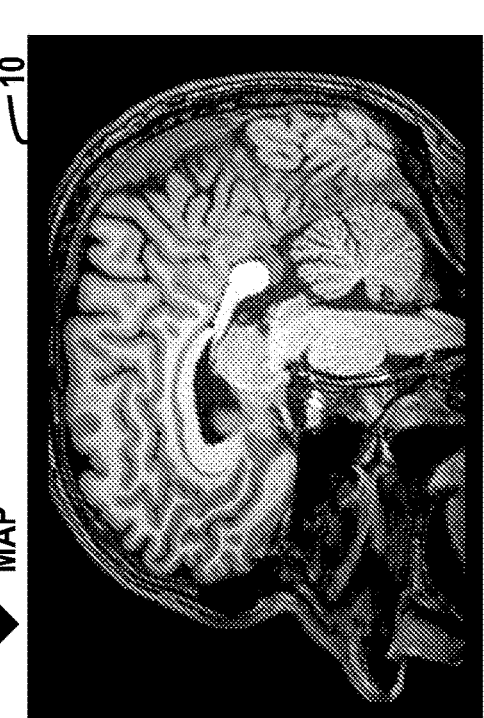

FIG. 14

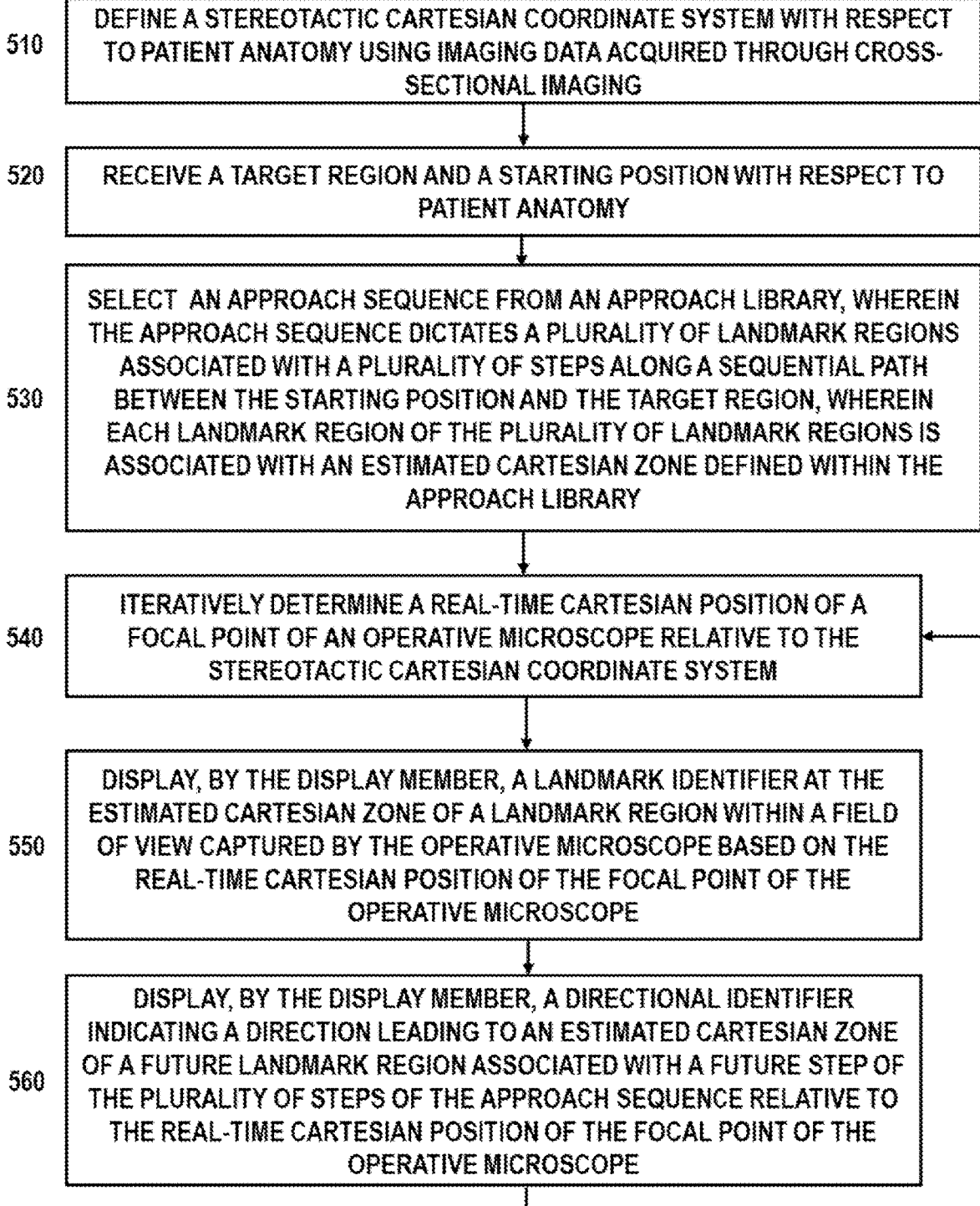

510 | DEFINE A STEREOTACTIC CARTESIAN COORDINATE SYSTEM WITH RESPECT TO PATIENT ANATOMY USING IMAGING DATA ACQUIRED THROUGH CROSS-SECTIONAL IMAGING

520 | RECEIVE A TARGET REGION AND A STARTING POSITION WITH RESPECT TO PATIENT ANATOMY

530 | SELECT AN APPROACH SEQUENCE FROM AN APPROACH LIBRARY, WHEREIN THE APPROACH SEQUENCE DICTATES A PLURALITY OF LANDMARK REGIONS ASSOCIATED WITH A PLURALITY OF STEPS ALONG A SEQUENTIAL PATH BETWEEN THE STARTING POSITION AND THE TARGET REGION, WHEREIN EACH LANDMARK REGION OF THE PLURALITY OF LANDMARK REGIONS IS ASSOCIATED WITH AN ESTIMATED CARTESIAN ZONE DEFINED WITHIN THE APPROACH LIBRARY

540 | ITERATIVELY DETERMINE A REAL-TIME CARTESIAN POSITION OF A FOCAL POINT OF AN OPERATIVE MICROSCOPE RELATIVE TO THE STEREOTACTIC CARTESIAN COORDINATE SYSTEM

550 | DISPLAY, BY THE DISPLAY MEMBER, A LANDMARK IDENTIFIER AT THE ESTIMATED CARTESIAN ZONE OF A LANDMARK REGION WITHIN A FIELD OF VIEW CAPTURED BY THE OPERATIVE MICROSCOPE BASED ON THE REAL-TIME CARTESIAN POSITION OF THE FOCAL POINT OF THE OPERATIVE MICROSCOPE

560 | DISPLAY, BY THE DISPLAY MEMBER, A DIRECTIONAL IDENTIFIER INDICATING A DIRECTION LEADING TO AN ESTIMATED CARTESIAN ZONE OF A FUTURE LANDMARK REGION ASSOCIATED WITH A FUTURE STEP OF THE PLURALITY OF STEPS OF THE APPROACH SEQUENCE RELATIVE TO THE REAL-TIME CARTESIAN POSITION OF THE FOCAL POINT OF THE OPERATIVE MICROSCOPE

FIG. 17

600

RECEIVE A SET OF CARTESIAN DATAPOINTS ASSOCIATED WITH A CARTESIAN POSITION OF A FOCAL POINT OF AN OPERATIVE MICROSCOPE AT A TIME STEP OF A PLURALITY OF TIME STEPS, WHEREIN THE SET OF CARTESIAN DATAPOINTS ARE DEFINED WITH RESPECT TO A STEREOTACTIC CARTESIAN COORDINATE SYSTEM

610

ASSIGN A CARTESIAN ZONE TO EACH RESPECTIVE LANDMARK REGION OF A PLURALITY OF LANDMARK REGIONS WITHIN A VIDEO CAPTURED BY THE OPERATIVE MICROSCOPE BASED ON THE CARTESIAN POSITIONS OF THE OPERATIVE MICROSCOPE AND FOCAL POINT

620

POPULATE AN APPROACH LIBRARY WITH THE SET OF CARTESIAN DATAPOINTS FOR THE SURGICAL CASE INCLUDING THE ASSIGNED CARTESIAN ZONES FOR THE PLURALITY OF LANDMARK REGIONS, WHEREIN EACH LANDMARK REGION IS ASSOCIATED WITH A PARTICULAR STEP OF THE APPROACH SEQUENCE

SYSTEMS AND METHODS FOR OPERATIVE MICROSCOPE TRACKING FOR TECHNICAL GUIDANCE

FIELD

The present disclosure generally relates to surgical guidance provided by a system educated through a library of stereotactic data attained throughout a multitude of duplicable surgical approach techniques, applicable to all cranial and spinal pathologies.

BACKGROUND

Cranial surgery possesses a unique anatomical feature that permits a stereotactic approach to the intracranial anatomy. This is facilitated by the rigid skull that permits mechanical fixation and subsequent external optical or magnetic sensory based registration of an individual patient's cross-sectional imaging (ex. Magnetic resonance imaging (MRI) or computed tomography (CT) scan). Following registration of the optical or magnetic tracking sensor, an instrument with a 3-dimensional optical tracking frame can be manipulated relative to the individual patient's cranial or spinal anatomy, permitting this instrument to appear in digital cartesian space and be represented relative to a digital display of the patient's anatomy. This technique, formally referred to as stereotactic navigation, has permitted surgeons to conduct anatomically precise techniques for years within cranial and spinal surgeries.

It is with these observations in mind, among others, that various aspects of the present disclosure were conceived and developed.

BRIEF DESCRIPTION OF THE DRAWINGS

FIG. 3 is a simplified diagram showing a data collection setup for the system of FIG. 2;

FIGS. 10A and 10B are each a diagram showing part of an approach log of the approach library of FIG. 5 for a particular surgical case;

FIG. 12 is a diagram showing a display member and an associated video image captured by an operative microscope of the system of FIG. 2 including landmark identifiers and directional identifiers of an approach sequence;

FIG. 14 is an illustration showing an approach selection process by the user interface of FIG. 13;

FIG. 17 is a process flow illustrating a process for providing technical guidance during a surgical case by the system of FIG. 2;

FIG. 18 is a process flow illustrating a process for populating an approach library of the system of FIG. 2;

Corresponding reference characters indicate corresponding elements among the view of the drawings. The headings used in the figures do not limit the scope of the claims.

DETAILED DESCRIPTION

The present disclosure includes a computer-implemented system that utilizes operating microscope focal point data defined within cartesian space for the purposes of surgical technical guidance, education, analytical evaluation, quality improvement, efficiency testing, and patient outcome assessment.

Introduction

The operating microscope has been a staple for microsurgical procedures and therefore frameless stereotactic navigation has been adopted to implement this instrument as a trackable device in Cartesian space relative to a patient's anatomy. To permit surgeon recognition of a focal point (i.e. convergence point of a left and right ocular vision within an operating microscope) the operating microscope outputs a focal point depth value relative to the tracked optical position of the operating room microscope's stereotactic registration frame. This permits a surgeon to view the focal point relative to the patient's anatomy. Given the surgeon is conducting a categorically reproducible microsurgical approach relative to the brain or spinal cord during operating room microscope use, the continuously tracked stereotactic position of the microscope relative to the patient in addition to the focal point depth relative to the microscope permits a mapping of a microsurgical approach trajectory relative to the patient's anatomy, as represented in a digital cartesian space occupied by the patient's cross-sectional imaging.

Stereotactic neuronavigation is a recent development within the field of neurosurgery, but has revolutionized the feasibility of micro-neurosurgical interventions. The ability to perform microneurosurgery remains a challenging endeavor requiring years of training and development of technical excellence. The operating microscope used to perform microdissection is tracked relative to the patient's brain, making a real-time assessment of microscope positioning a feasible task.

Figure 1:
FIG. 1 is a cross-sectional image of a cranium indicating a surgical approach between a target region and a starting position.
Figure 2:
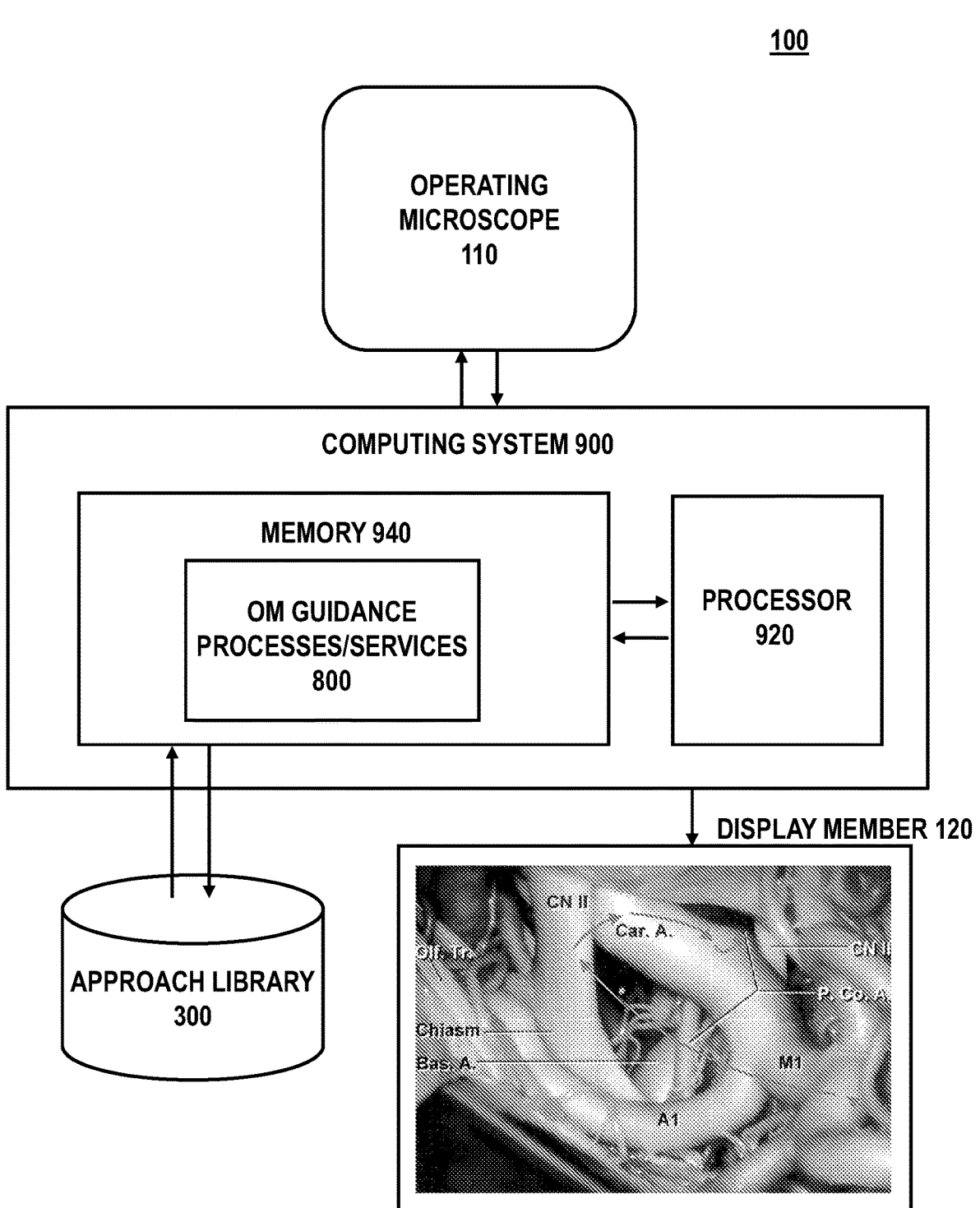
FIG. 2 is a simplified diagram showing a system for operating microscope (OM) tracking.
Figure 4:
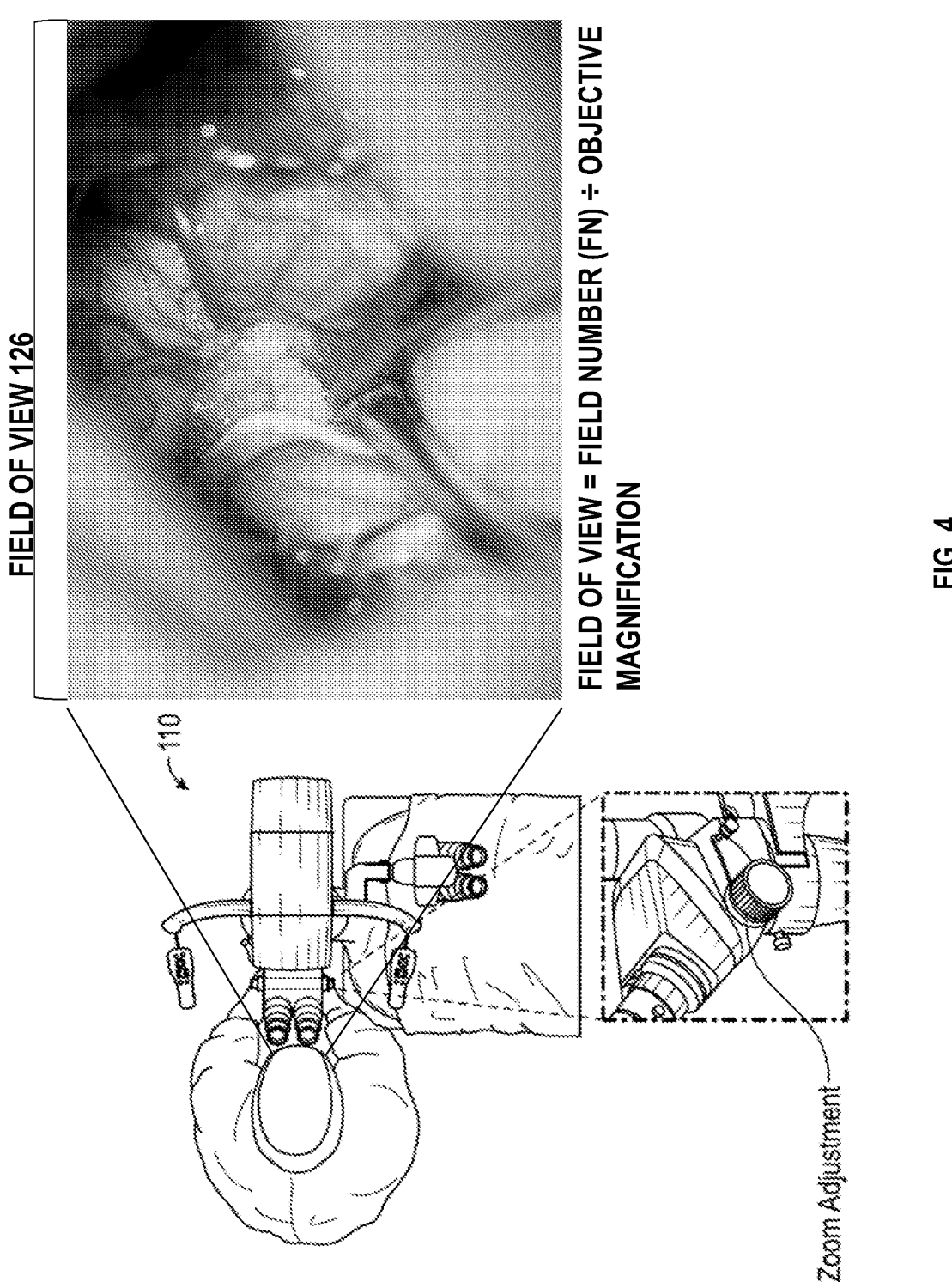
FIG. 4 is a simplified diagram showing a field of view of an operating microscope of the system of FIG. 2.

A system of the present application enables a computer-implemented rendered visualization of a surgeon's path or "roadmap" to a particular target region during a surgical case. Referring directly to FIGS. 1-3, the system 100 includes a computing system 900 in operative communication with an operating microscope (OM) 110 and a display member 120. The computing system 900 communicates with an approach library 300 that includes data related to various surgical approach sequences, or "roadmaps" to various target regions. The approach library 300 can be populated by the system 100 and analyzed for variance and trends, as well as provide instruction and guidance through the display member 120 during a surgical case. The computing system 900 includes an OM Guidance Processes/Services application 800 to collect surgical approach data using the operating microscope (OM) 110 to populate the approach library 300. In another aspect, the OM Guidance Processes/Services application 914 can also provide direct or indirect guidance to a practitioner during a surgical case through the display member 120 based on a real-time position of a focal point of the OM 110.

Referring to FIGS. 1-5, prior to data collection or intraoperative guidance during a surgical case, patient anatomy is first registered with a stereotactic navigation system 130 of the system 100. As shown in FIG. 3, a stereotactic frame 30 associated with the stereotactic navigation system 130 provides four stereotactic reference points 218 to orient the patient. These registration points are also used as reference within a corresponding approach log 340 (FIG. 6) which will be discussed in greater detail below. The stereotactic navigation system 130 defines a stereotactic Cartesian coordinate system with respect to patient anatomy using imaging data 10 acquired through one or more cross-sectional imaging techniques.

Populating Approach Library

Figure 5:
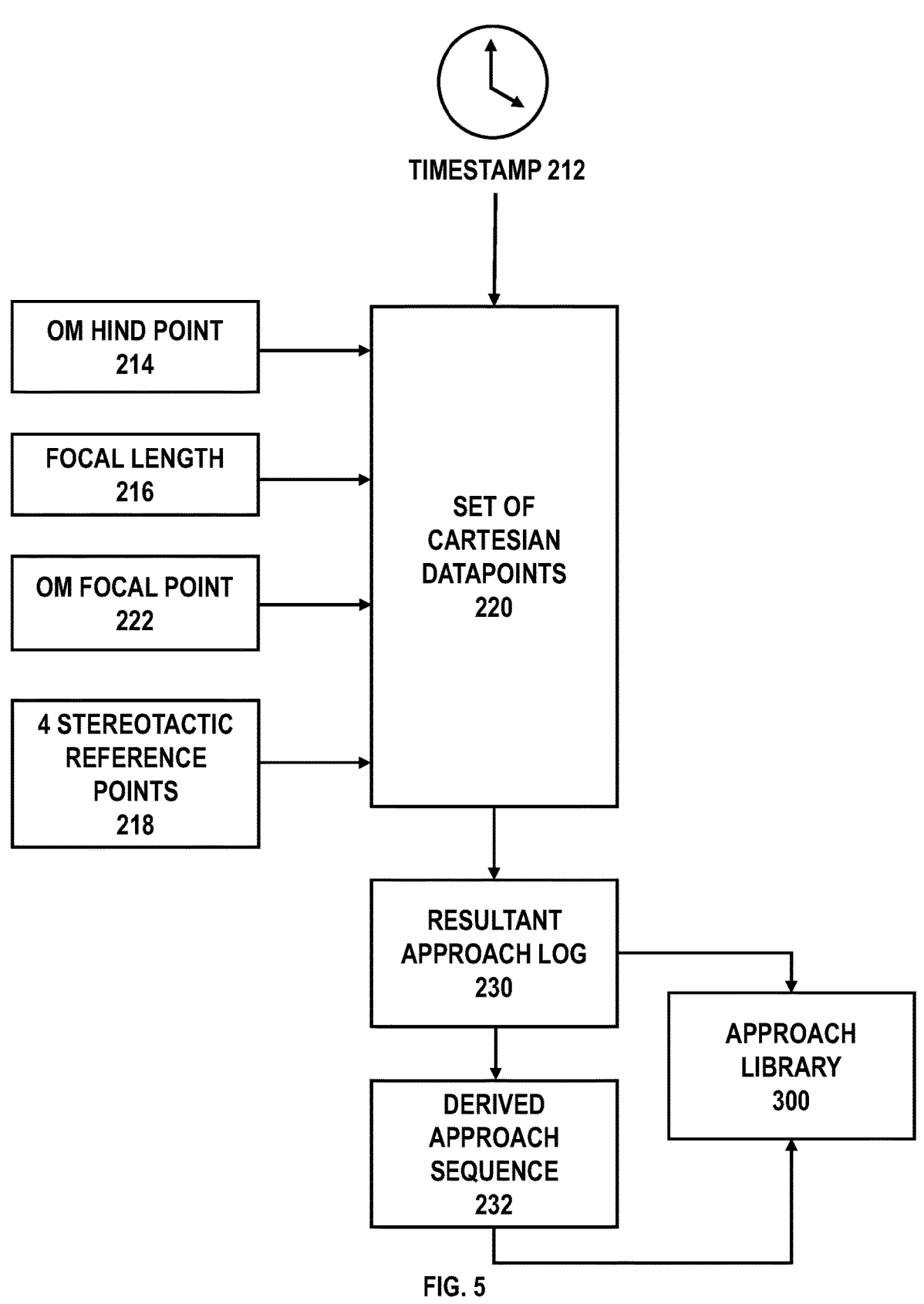
FIG. 5 is a simplified diagram showing generation of an approach log and derived approach sequence of the system of FIG. 2.
Figure 6:
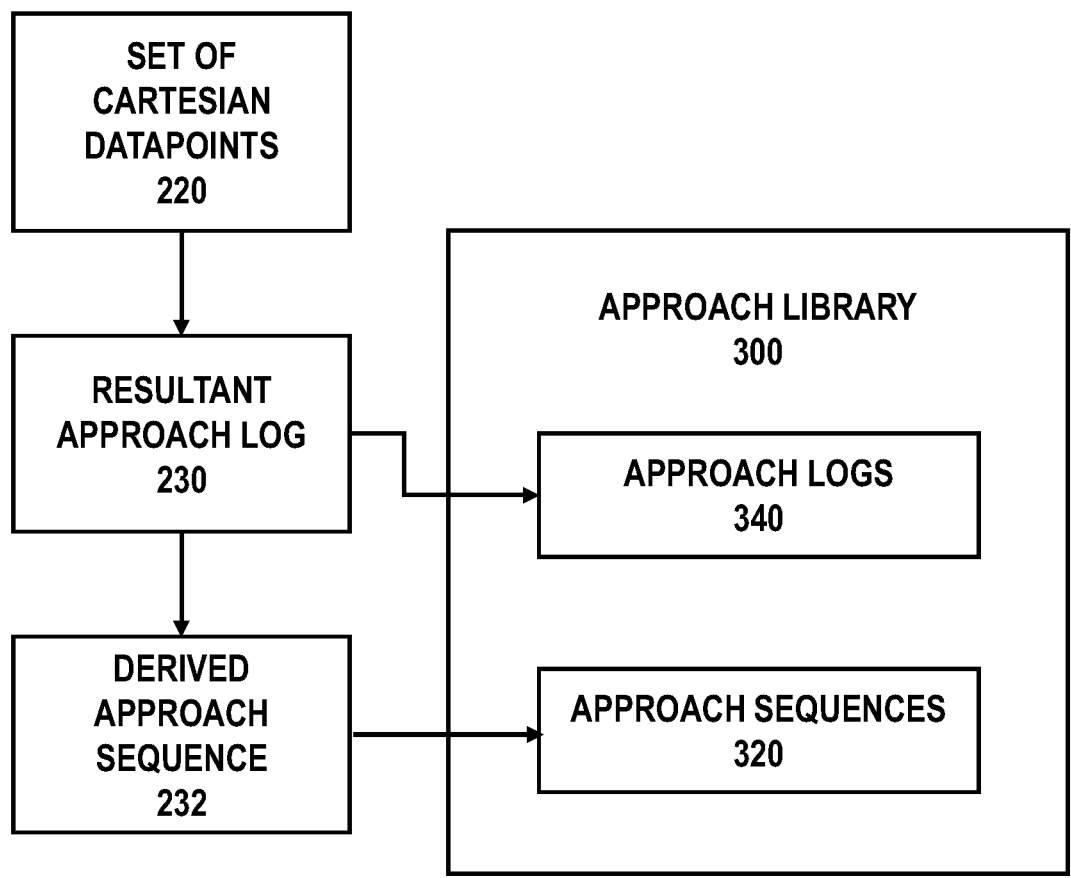
FIG. 6 is a simplified diagram showing population of the approach library based on the approach log and derived approach sequence of the system of FIG. 2.

Referring to FIGS. 3-10B, the OM 110 communicates a recorded OM focal point 222 including x, y, and z Cartesian positional coordinate data in Cartesian space to the computing system 900 as the surgeon progresses along an approach sequence of a surgical case. As shown in FIG. 5, the system 100 records a Cartesian position of an OM hind point 214 in addition to the focal point 222 of the OM 110 relative to the stereotactic Cartesian coordinate system defined during registration of patient anatomy. The system 100 records and timestamps the advancement of the focal point 222 of the OM 110 and other Cartesian coordinate data represented within the set of Cartesian datapoints to record a resultant approach log 230 representative of a derived approach sequence 232 for the surgical case. In particular, the system 100 records the set of Cartesian data points 220 within the approach log 230 at a timestamp 212 of a plurality of timestamps 212 that are indicative of the location of the focal point 222 of the OM 110 within an approach log 340 during the surgical case. In some embodiments, the OM 110 can record video or image data of a field-of-view of the OM 110 including the focal point, in addition to the set of Cartesian data points 220. As shown in FIG. 6, the resultant approach log 230 is then populated into the approach library 300 as a single approach log 340 of a plurality of approach logs 340; similarly, the derived approach sequence 232 is populated into the approach library 300 as a single approach sequence 320 of a plurality of approach sequences 320. Tracking a focal point 222 of the OM 110 over multiple repetitions of various cranial surgical exposures and approaches permits the system 100 to generate an approximation of the surgical pathway or roadmap by which a surgeon must navigate the brain or another bodily structure to achieve a goal, such as clipping an aneurysm or resecting a tumor.

The set of cartesian data points 220 collected throughout a surgical case can be reviewed postoperatively to understand the surgical path taken and the method by which the surgeon approached the target area. The data collected by the system 100 can be studied to identify shortcomings and delays in the surgical approach. The resultant approach log 230 captured by the system 100 in the form of one or more sets of Cartesian data points 220 can be analyzed to extract the derived approach sequence 232 followed during the surgical case including a landmark listing 334 (FIG. 8) and one or more actions taken along the derived approach sequence 232. Following the population of the approach library 300 with a plurality of approach logs 340 across a plurality of surgical cases, the system 100 enables the formation of approach modules and "master surgeon" templates for various approaches which could preoperatively prepare a surgeon for the procedure, or serve as an intraoperative guide.

One example of this idea is demonstrated in FIG. 1. The cartesian coordinates from the "intraoperative data" could be overlaid over cross-sectional image data 10 or a 3D representation of patient imaging to permit the surgeon to visualize the surgical path of approach necessary to achieve during the surgery. In the specific example of FIG. 1, the pineal region would have been explored with a resultant set of cartesian data points 220 representing this path.

Figure 8:
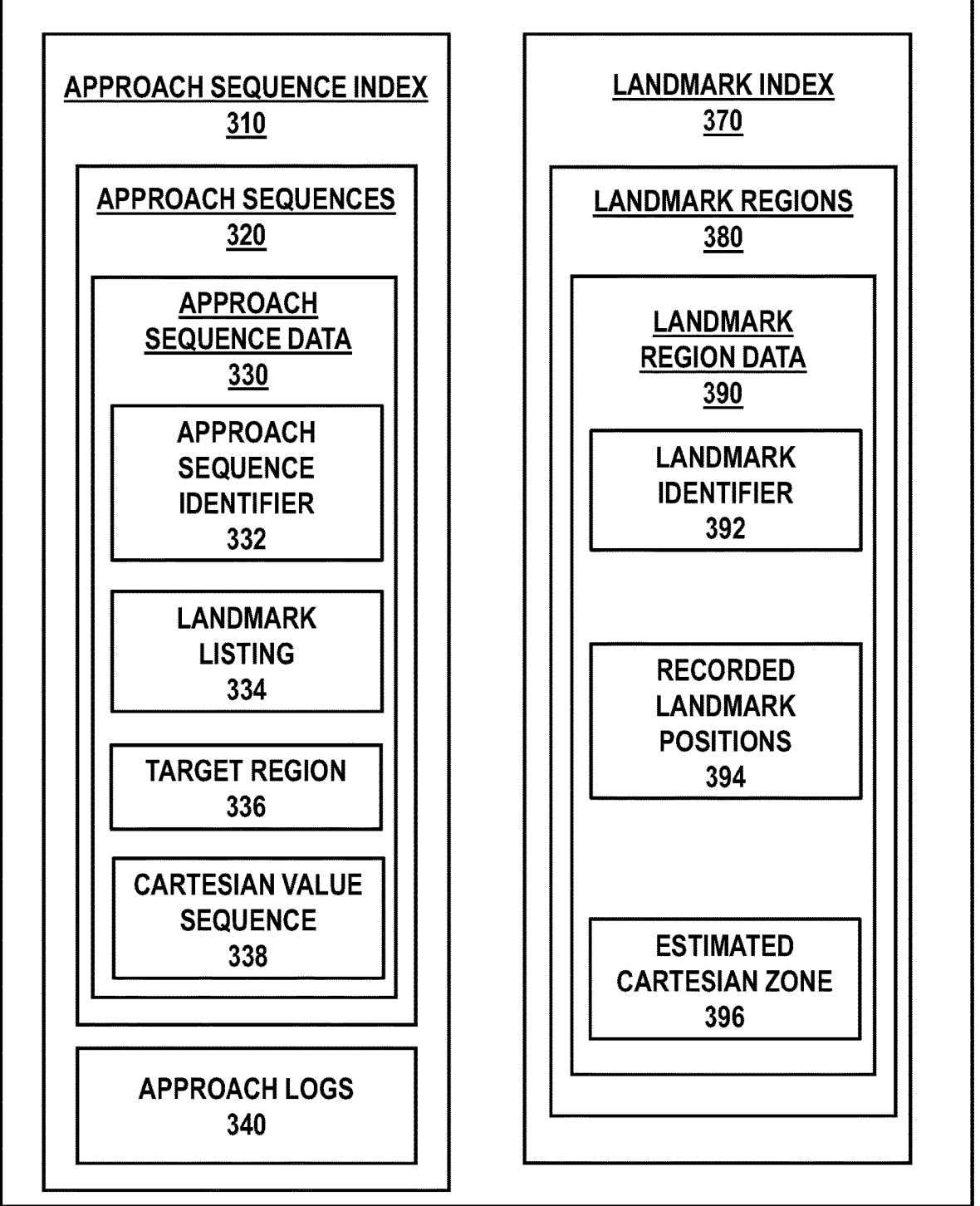
FIG. 8 is a simplified diagram showing an approach library of the system of FIG. 2.
Figure 9:
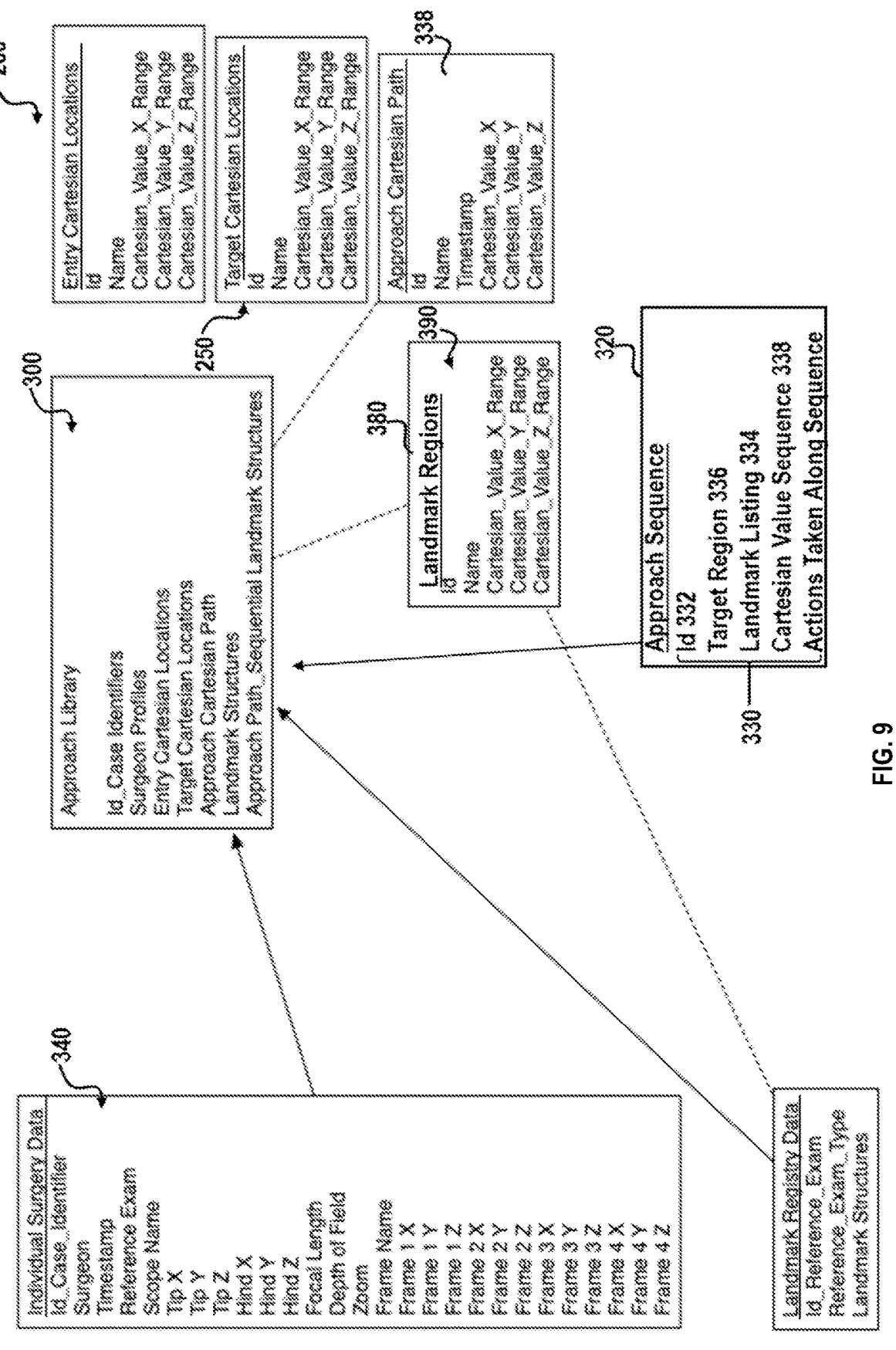
FIG. 9 is a database diagram showing components of the approach library of FIG. 5 and the selected target region and starting position of FIG. 8.

Referring to FIGS. 8 and 9, an approach sequence 320 categorized within the approach library 300 and followed by the practitioner during collection of the set of Cartesian data points 220 can be characterized as a plurality of steps along a sequential path between a starting position and a target region. Each step along the sequential path is associated with a respective landmark region 380 of a plurality of landmark regions 380. Each landmark region 380 is associated with an estimated cartesian zone 396 relative to patient anatomy and is defined within the approach library 300. Each step in the approach sequence 320 is also associated with directions to a next landmark region 380 of the approach sequence 320. Annotation of such can be helpful for practitioners when communicating approach strategies or when making preoperative or intra-operative decisions. The approach library 300 of the system 100 aims to categorically organize the plurality of approach sequences 320 extracted from a plurality of approach logs 340 based on various characteristics of each approach sequence 320. Each approach log 340 of the plurality of approach logs 340 captured by the system 100 in the form of a Cartesian value sequence 338 corresponds with an approach sequence 320 followed during the surgical case including a landmark listing 334 and one or more actions taken along the approach sequence 320. The landmark listing 334 can include a plurality of landmark regions 380 encountered during the approach sequence 320. In some embodiments, the approach library 300 includes landmark region data 390 for each individual landmark region 380 that encompasses a plurality of recorded landmark positions 394 across a plurality of surgical cases.

Figure 7:
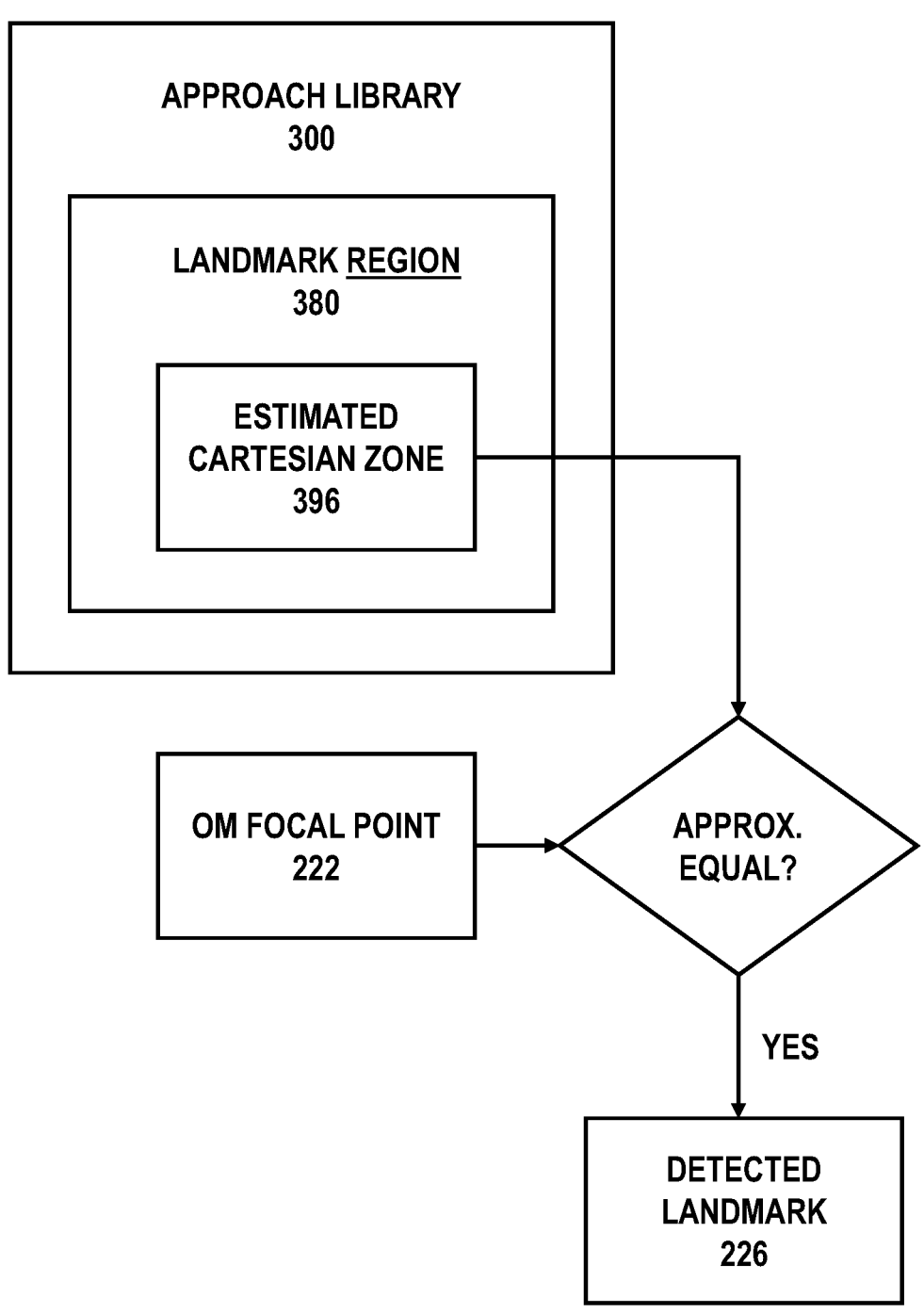
FIG. 7 is a simplified diagram showing identification of a detected landmark based on the focal point of the OM of FIG. 2.

The system 100 tracks the focal point of the OM 110 over multiple repetitions of various surgical exposures and approaches. Data collected by the system 100 using the OM 110 permits the population of the approach library 300 which can in turn be referenced by the system 100 when providing intraoperative guidance to a practitioner. The approach library 300 includes categorically organized approximations of a surgical pathway for a plurality of approach sequences 320 by which a surgeon must navigate the brain to achieve access to a target anatomical region, such as an aneurysm or tumor. To enhance the usefulness of the approach library 300, as is relevant to surgical approach technique, the approach library 300 includes a landmark index 370 that defines a respective estimated Cartesian zone 396 for each landmark region 380 of the plurality of landmark regions 380 represented within the landmark index 370 to represent an approach sequence 320 as an associative traversing of landmark regions 380. An example for this is a cranial approach to the posterior communicating artery for an aneurysm clipping procedure, shown in FIG. 12. This surgical approach requires the successful navigation along an approach sequence 320 of some landmark regions 380 of the plurality of landmark regions 380, as follows:

a. M4—Middle cerebral artery (M4 Segment)
  b. M3—Middle cerebral artery (M3 Segment)
  c. M2—Middle cerebral artery (M2 Segment)
  d. M1—Middle cerebral artery (M1 Segment)
  e. A1—Anterior cerebral artery (A1 Segment)
  f. CNII—Cranial Nerve II (Optic Nerve)
  g. C6—Internal Carotid Artery (Ophthalmic Segment)
  h. C7—Internal Carotid Artery (Communicating Segment)
  i. Posterior Communicating Artery Aneurysm For this approach sequence 320 of the plurality of approach sequences 320, the nomenclature of a landmark listing 334 including sequential anatomical landmarks could be represented as: M4-M3-M2-M1-A1-CNII-C6-C7. Locations M3, M2, M1, A1, CNII, C6 and C7 are visible within the single field-of-view 126 displayed on the display member 120 in FIG. 12. The surgeon first obtains a stereotactically-based Cartesian registration of patient anatomy in digital space during the enactment of this workflow. The approach library 300 is populated by both the generic stereotactic pathway along this anatomy relative to the patient's cross-sectional imaging. In some embodiments, the system 100 can accept manual or machine-identified designations of Cartesian zones along this Cartesian pathway that represent landmark regions 380. The manual or machine-identified designation of Cartesian zones will generate nomenclature for sequential landmark regions 380 in the form of a landmark listing 334 replicatively relevant to a given categorically designated surgical approach sequence 320 within the approach library 300. Applying one or more machine learning techniques to a dataset that includes one or more manually designated Cartesian zones for landmark regions 380 can allow for automated assignment of Cartesian zones without the use of laborious manual designation.
Identification of Landmark Regions:

Referring to FIGS. 7 and 8, the system 100 identifies a detected landmark region 226 of the plurality of landmark regions 380 based on a recorded location of the focal point 222 of the OM 110. In particular, the system 100 identifies a landmark region 380 as encountered when a Cartesian position of the focal point 222 of the OM 110 as recorded in the approach log 340 is approximately equal to, or contained within, the estimated Cartesian zone 396 of the landmark region 380 as dictated by the approach library 300. The system 100 recognizes that the landmark region 380 within the approach library 300 has been encountered based on a recorded landmark position 394 at which the focal point 222 of the operating microscope 110 overlaps with the estimated Cartesian zone 396.

Following recordation of the approach log 340 for a surgical case, the system 100 can assign an estimated Cartesian zone 396 of patient anatomy to each respective landmark region 380 captured by the focal point of the OM 110 based on the Cartesian position of the focal point. Each landmark region 380 stored within the approach library 300 is associated with a respective estimated Cartesian zone 396 relative to patient anatomy in which the landmark region 380 is estimated to be present. In some embodiments, the estimated Cartesian zone 396 is a volumetric range calculated based on a plurality of recorded landmark positions 394 recorded across a plurality of approach logs 340. As the individual approach log 340 captured for a surgical case can provide an additional recorded landmark position 394 for each landmark region 380 encountered, the system 100 is operable to update an estimated Cartesian zone 396 for each landmark region 380 encountered based on the additional recorded landmark position 394. In some embodiments, additional data filtering operations can be applied to ensure accuracy of the estimated Cartesian zones 396. The system 100 populates the approach library 300 with approach sequence data 330 and a recorded landmark position 394 for each landmark region 380 encountered within the approach sequence 320.

Referring to FIGS. 5, 6 and 8, the system records time-stamped Cartesian focal point position data 222 obtained by the operating microscope 110 when traversing from a starting position to a target region during a surgical case as an approach log 340 of a plurality of approach logs 340. Each approach log 340 is descriptive of an approach sequence 320 of a plurality of approach sequences 320. In some embodiments, the approach library 300 can associate one or more approach logs 340 with a single approach sequence 320, to account for natural variations in anatomy and surgical technique across a plurality of recorded approach logs 340. The approach sequence 340 is descriptive of an appropriate surgical route from the starting position to the target structure including a plurality of steps. It should be noted that while two approach sequences 340 can include the same starting position and the same target structure, the intermediate "route" taken as represented by the landmark regions 380 encountered or directions taken during each respective approach sequence 340 can differ. In some embodiments, the system 100 associates each step of the approach sequence 320 with a respective landmark region 380. Each approach sequence 320 stored within the approach library 300 can include approach sequence data 330 that includes an associated approach sequence identifier 332, the landmark listing 334, a target region 336 at which the approach sequence 320 terminates, and a Cartesian value sequence 338. The Cartesian value sequence 338 can be an averaged sequence of Cartesian values obtained based on a plurality of approach logs 340 that describe the same approach sequence 320. In other embodiments, additional techniques can be applied to data from the approach logs 340 to produce a "master template" Cartesian value sequence 338 associated with the approach sequence 320 based on the approach logs 340. In some embodiments, the Cartesian value sequence can be directly selected from one or more approach logs 340 that follow the approach sequence 320. Further, approach logs 340 can be categorically organized within the approach library 300 using characteristics including surgeon, location, approach sequence, and/or patient demographics (age, sex, condition).

In some embodiments, the system 100 enables a practitioner to manually identify or otherwise verify one or more landmark regions 380 encountered within a surgical case. Video or image data of a field-of-view captured by the OM 110 can accompany the set of Cartesian datapoints 220, and a practitioner reviewing the video or image data can identify one or more recorded landmark positions 394 at a selected timestamp for one or more respective landmark regions 380 within the approach sequence 320. The system 100 extracts one or more recorded landmark positions 394 at the Cartesian position of the focal point of the OM 110 at the selected timestamp within the video or image data.

Figure 13:
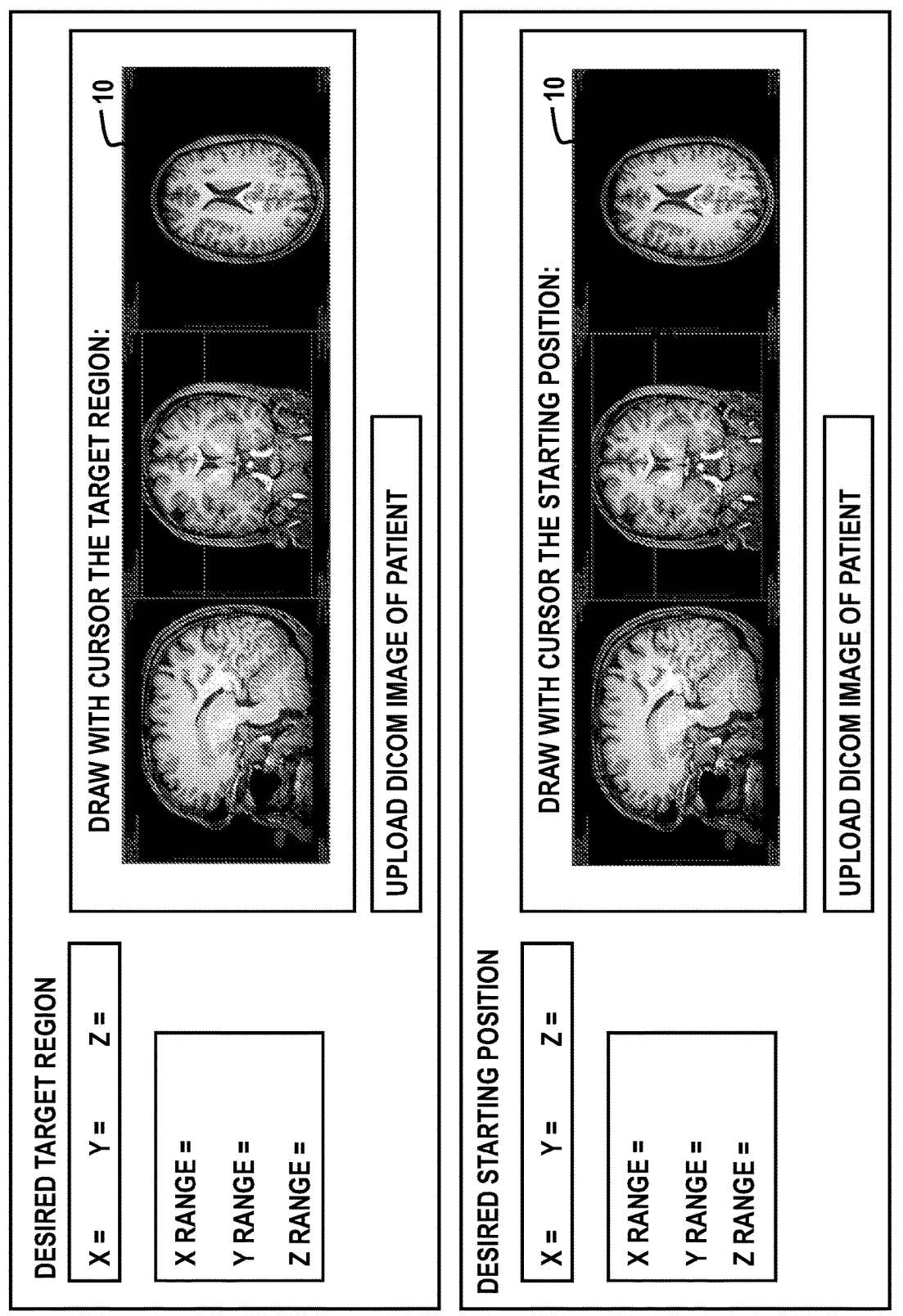
FIG. 13 is an illustration showing a user interface of the system of FIG. 2.

Referring to FIG. 13, in some embodiments the system 100 can apply one or more machine learning techniques for classifying anatomical zones within imaging data to aid in identifying landmark regions 380 encountered during the surgical case. In particular, the system 100 assigns the estimated Cartesian zone 396 to each respective landmark region 380 captured at the focal point of the operative microscope during a surgical case using the one or more machine learning techniques based on patient anatomy. In some embodiments, elements of a machine learning module can be trained using a dataset that includes one or more manually assigned estimated Cartesian zones.

Aspects of the landmark index 370 of the approach library 300 can additionally be populated using cross-sectional imaging techniques. In particular, a stereotactic Cartesian coordinate system can be defined with respect to one or more cross-sectional images. The system 100 can identify landmark regions 380 and extract corresponding landmark region data 390 including a recorded landmark position 394 through cross-sectional images 10 to populate the landmark index 370 of the approach library 300. In some embodiments, this is achieved through manual mesh segmentation of the Cartesian space to indicate the volumes of Cartesian space assigned to a particular landmark region 380, and can further be aided by one or more machine learning techniques implemented by the system 100. In some embodiments, the cross-sectional images 10 are Digital Imaging and Communications in Medicine (DICOM) images. An advantage of this method would be the collection of anatomical location data for the plurality of landmark regions 380 without surgery, or to enable pre-registration of estimated Cartesian zones 396 that are patient-specific prior to execution of a surgical case.

Referring to FIG. 18, a process flow 600 is illustrated showing a method for populating the approach library 300. At block 610, the processor 920 receives the set of Cartesian data points 220 associated with the Cartesian position of the focal point 222 of the OM 110 at a timestamp 212 of a plurality of timestamps 212, wherein the set of Cartesian data points 220 are defined with respect to a stereotactic Cartesian coordinate system. At block 620, the processor 920 assigns an estimated Cartesian zone 396 to each respective landmark region 380 of a plurality of landmark regions 380 within a video captured by the OM 110 based on the cartesian positions of the OM 110 and focal point 222. At block 630, the processor 920 populates an approach library 300 with the set of Cartesian datapoints 220 for the surgical case including the estimated Cartesian zones 396 for the plurality of landmark regions 380, wherein each landmark region 380 is associated with a particular step of the approach sequence 320.

Intraoperative Guidance

Referring to FIGS. 2, 3, 5-7 and 11-16, the system 100 is operable to provide direct or indirect guidance to a practitioner during a surgical case through the display member 120 based on a real-time position of a focal point 222 of the operating microscope 110. In a preferred embodiment, the system 100 references the approach library 300 to identify one or more selected approach sequences 270 based on a provided target region 250. The system 100 is further operable to annotate a field-of-view 126 of the operating microscope 110 displayed on the display member 120 with one or more landmark identifiers 122 indicating a landmark region 380 relative to patient anatomy, as shown in FIG. 12.

Further, the system 100 is operable to annotate the field-of-view 126 on the display member 120 with one or more directional identifiers 124 indicating a direction leading to a future landmark region 380 of an approach sequence 320.

Following the population of the approach library 300 as discussed above and categorically organized based on the combination of anatomical starting position and trajectory as defined in Cartesian space, the approach library 300 can then be queried based on a manually-designated target region 250. In some embodiments, the system 100 requires a user to select a categorically relevant target region 250 or draw a target region 250 within a 3-D digital space, as shown in the example user interface of FIGS. 15 and 16. This reference can then be queried against the approach library 300 to identify one or more selected approach sequences 270 of the plurality of approach sequences 320 and output the associated content.

In some embodiments, the output content can include a (1) raw stereotactic cartesian dataset in the form of a selected approach log 280 of the plurality of approach logs 340 or a stereotactic cartesian value sequence 338 averaged over a multitude of approach logs 340 within the approach library 300, and (2) a listing of one or more landmark regions 272 for a selected approach sequence 270 of the plurality of approach sequences 320 to the target region 250. The output can be visualized in a computer generated digital 3-D space on an external display member 120 for the purpose of preoperative planning for example, or can be displayed within a heads-up display (HUD) of the OM 110 to inform the surgeon of the appropriate sequential regional anatomy or Cartesian path necessary to reach the target region 250. Within the display member 120 (either a monitor or operative microscope HUD rendition of the surgical approach map) the data could be presented in a guidance manner, including directional identifiers 124 in the form of arrows for Cartesian space guidance or highlights of Cartesian zones and associated landmark identifiers 122 for relevant surgical anatomy can be displayed actively on the display member 120 as the surgeon traverses the anatomy relevant to the selected approach sequence 270. The system 100 enables real-time adaptation to a current Cartesian location of the OM 110 and provides relevant input to guide the surgical approach based on the data stored in the approach library 300.

In some embodiments, the system 100 is operable to adjust a position of the OM 110 to focus on the focal point of interest at a specified approach angle. The approach angle is defined by an approach axis 224 (FIG. 3) which is a line that intersects the focal point 222 and the hind point 214. An approach axis 224 defined for a landmark region 380 that was recorded within a previously-recorded approach log 340 a past surgical case can be used by the system 100 to orient the OM 110 in the exact same direction in space.

In one aspect, the system 100 receives a selection of a landmark region 380 from the plurality of landmark regions 380 in the approach library 300. The system 100 can then output a directional indicator 124 and/or laser guidance indicator to indicate the direction to go to reach the associated estimated Cartesian zone 396, within the broader scope of the path described by the selected approach sequence 270. In a similar way, the system 100 is operable to align the OM 110 with a previously-recorded focal point 222 and hind point 214 combination (that together define the approach axis 224) to show a surgeon where the landmark region 380 is located. This concept could allow the approach library 300 to "modify" the course from a current location of the OM focal point 222 to the landmark region 380 as a new target structure.

In some embodiments, surgeon-specific "profiles" or "master templates" can be generated following the recording of expansile datasets for a given surgeon's cranial approach techniques. Therefore, the approach library 300 can be categorically organized to permit the user to select from surgeon-specific profiles of interest to one or more selected approach sequences 270 and selected approach logs 280 that are relevant to a surgical approach as performed by a particular surgeon.

The data housed within the approach library 300 permit export of educational endeavors as a novel learning resource. With this intent in mind, the selected approach logs 280 can also be exported with time-code corresponding to a surgical video captured by the OM 110 during the stereotactic cartesian recording to allow a user to navigate a surgical video with a timeline. The denotation of landmark regions 380 encountered during the recording can be used as a bookmark or "table of contents" for surgical videos, such that in a three-dimensional or multi-dimensional viewing window within the system 100, a surgeon can click on a specific anatomical region where a focal point of the OM 110 has been tracked and thereby be efficiently navigated to the corresponding timepoint within the surgical video during which the Cartesian coordinate of the focal point was tracked.

Figure 11:
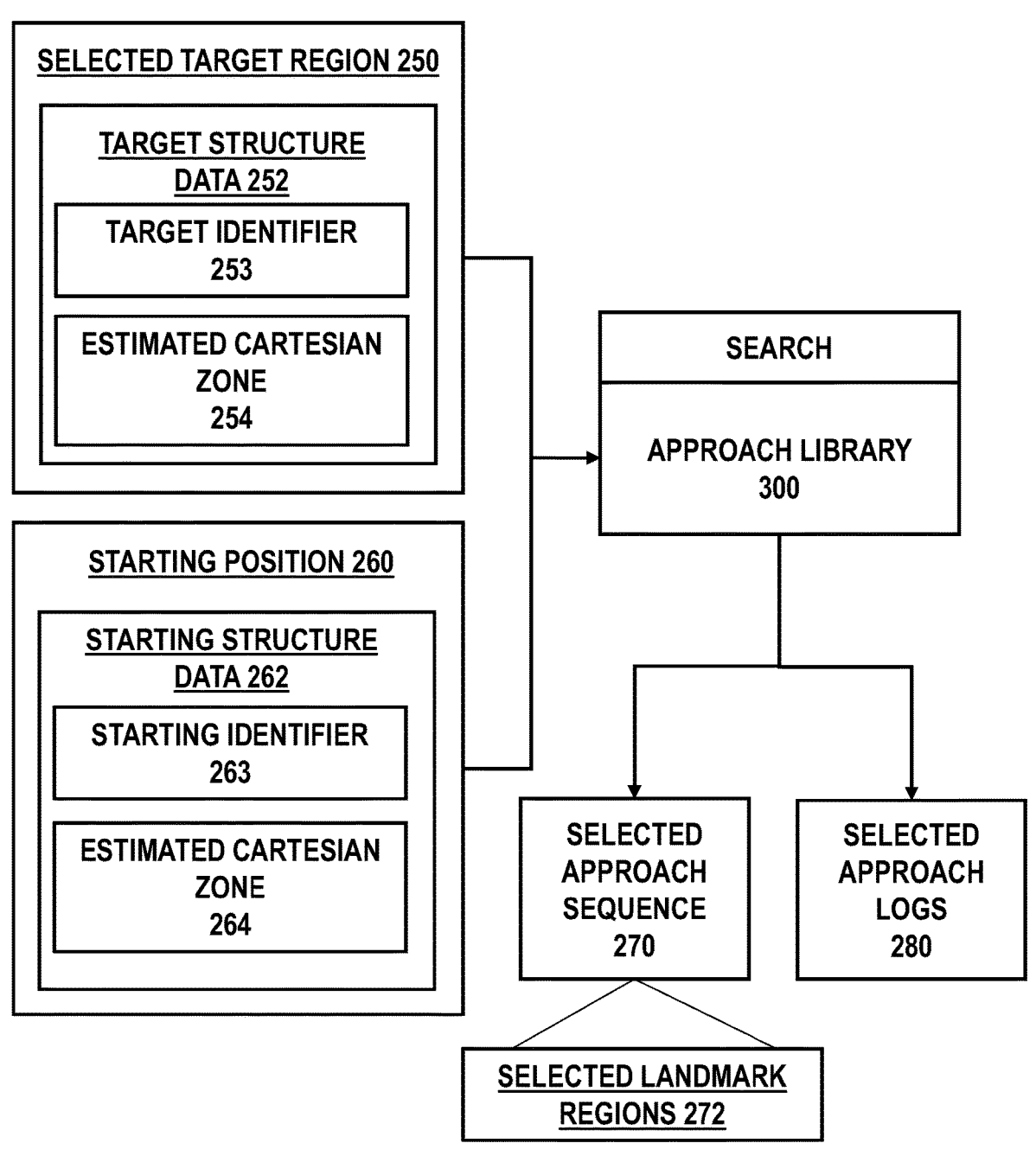
FIG. 11 is a simplified diagram showing retrieval of approach results based on a selected target region and starting position from the approach library of FIG. 7.

In some embodiments, as shown in FIGS. 11, 13 and 14, the system 100 receives a selected target region 250 through a user interface 400 by highlighting one or more pixels in a cross-sectional image 10 that correspond to a Cartesian position as defined within the stereotactic Cartesian coordinate system relative to patient anatomy. The Cartesian positions of the one or more pixels are taken as the estimated cartesian zone 254 of the target region 250.

In other embodiments, the target region 250 can be selected from a listing of landmark regions 380 within the approach library 300 associated with the patient. The system 100 can identify various landmark regions 380 and patient-specific recorded landmark positions 394 using cross-sectional image data 10 associated with the patient, and in some embodiments select a target region 250 from the patient-specific recorded landmark positions 394.

In some embodiments, the starting position 260 can be selected in a similar manner to the target region. As shown, in the user interface, the starting position can be selected by highlighting one or more pixels in a cross-sectional image 10 or 3-D model that correspond to a cartesian position as defined within the stereotactic Cartesian coordinate system relative to patient anatomy. The Cartesian positions of the one or more pixels are taken as the estimated cartesian zone 264 of the starting position 260. In other embodiments, the starting position can be one of a plurality of starting positions recommended by the system 100 based on the target region 250 if more than one approach sequence 320 stored within the approach library 300 can be recommended for the target region 250. In the case of such, a surgeon can select a recommended starting position 260.

The system 100 queries the approach library 300 to identify one or more selected approach sequences 270 indicative of the sequential path between the starting position 260 and the target region 250 based on data stored in the approach sequence index 310 and the landmark index 370 of the approach library 300. As discussed above, the plurality of approach sequences 320 are categorically organized within the approach sequence index 310. As a result, the system 100 can present one or more selected approach sequences 270 from the plurality of approach sequences 320 stored in the approach sequence index 310.

A selected approach sequence 270 dictates a plurality of selected landmark regions 272 of the plurality of landmark regions 380 associated with a plurality of steps along a sequential path between the starting position 260 and the target region 250. Each selected landmark region 272 of the plurality of landmark regions 380 is associated with an estimated Cartesian zone 396 defined within the approach library 300.

It should be noted that in some embodiments, the system 100 can present one or more selected approach sequences 270 that do not necessarily terminate in the target region 250, the selected approach sequence 270 simply needs to include the selected target region 250 as a selected landmark region 272 in order to be considered. Additionally, in some embodiments, the system 100 can also accept multiple "stops" and can piece together one or more sections of one or more approach sequences 320 within the approach library 300 to result in a selected approach sequence 270 that is piecewise in nature.

In some embodiments, the system 100 can provide one or more selected approach logs 280 that correspond with the one or more selected approach sequences 270 for direct or indirect guidance. The selected approach logs 280 can be taken directly from the plurality of approach logs 340 from the approach sequence index 310, Selected approach logs 280 can each include a corresponding set of Cartesian data points 220 including a plurality of Cartesian datapoint instances associated with a Cartesian position of a focal point of an operative microscope recorded throughout a previously-recorded surgical case of a plurality of previously-recorded surgical cases, wherein the set of Cartesian datapoints are recorded at each time step of a plurality of time steps throughout the surgical case. Such an example of an approach log 340 is shown in FIGS. 10A and 10B. In some embodiments, the system 100 can additionally display one or more indirect guidance materials available for the selected approach sequence (e.g. videos captured during other surgical cases that follow the approach sequence, literature regarding the approach, etc).

Direct Intraoperative Guidance

Figure 15:
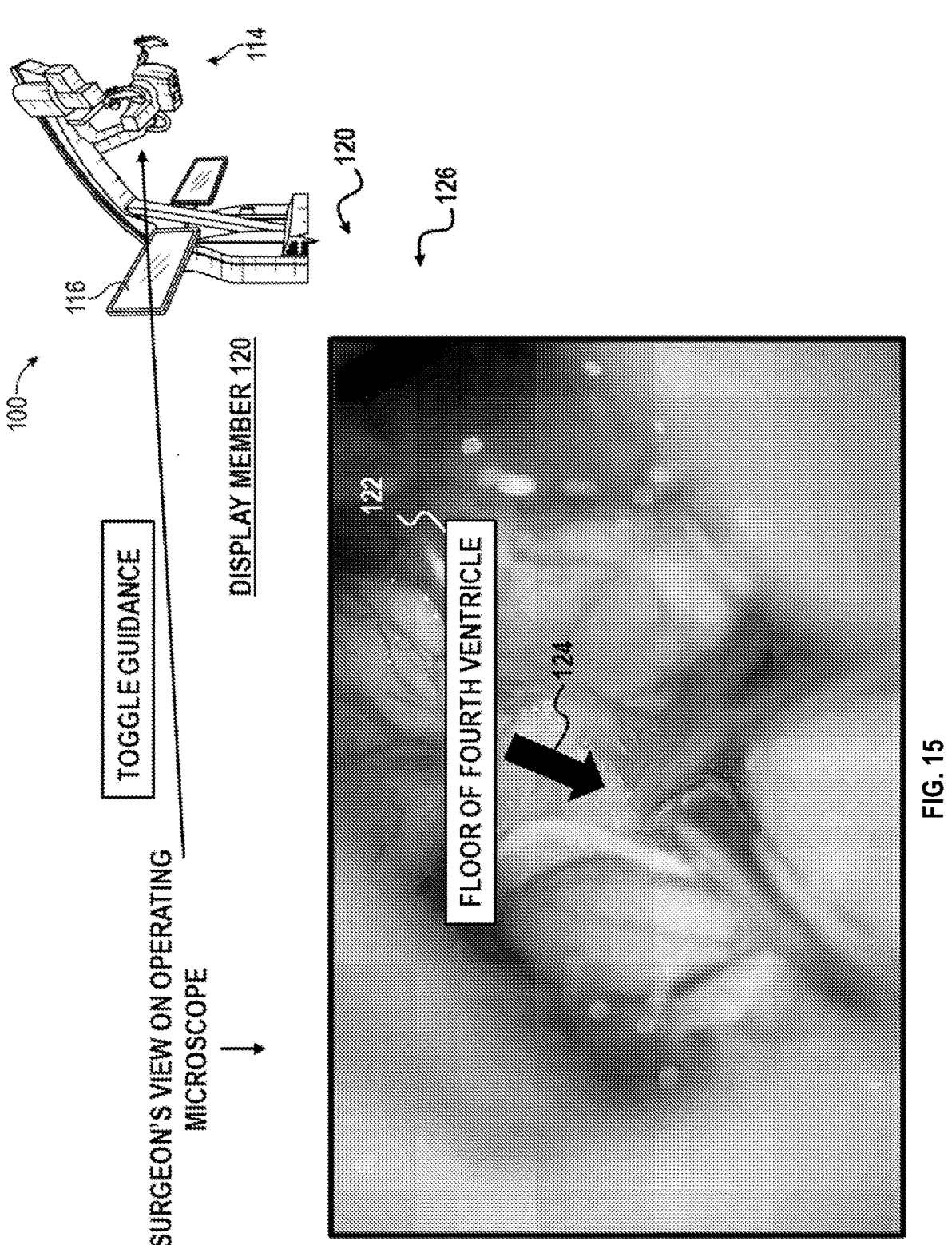
FIGS. 15 and 16 are illustrations showing a surgeon's view using the operative microscope with the system of FIG. 2.
Figure 16:
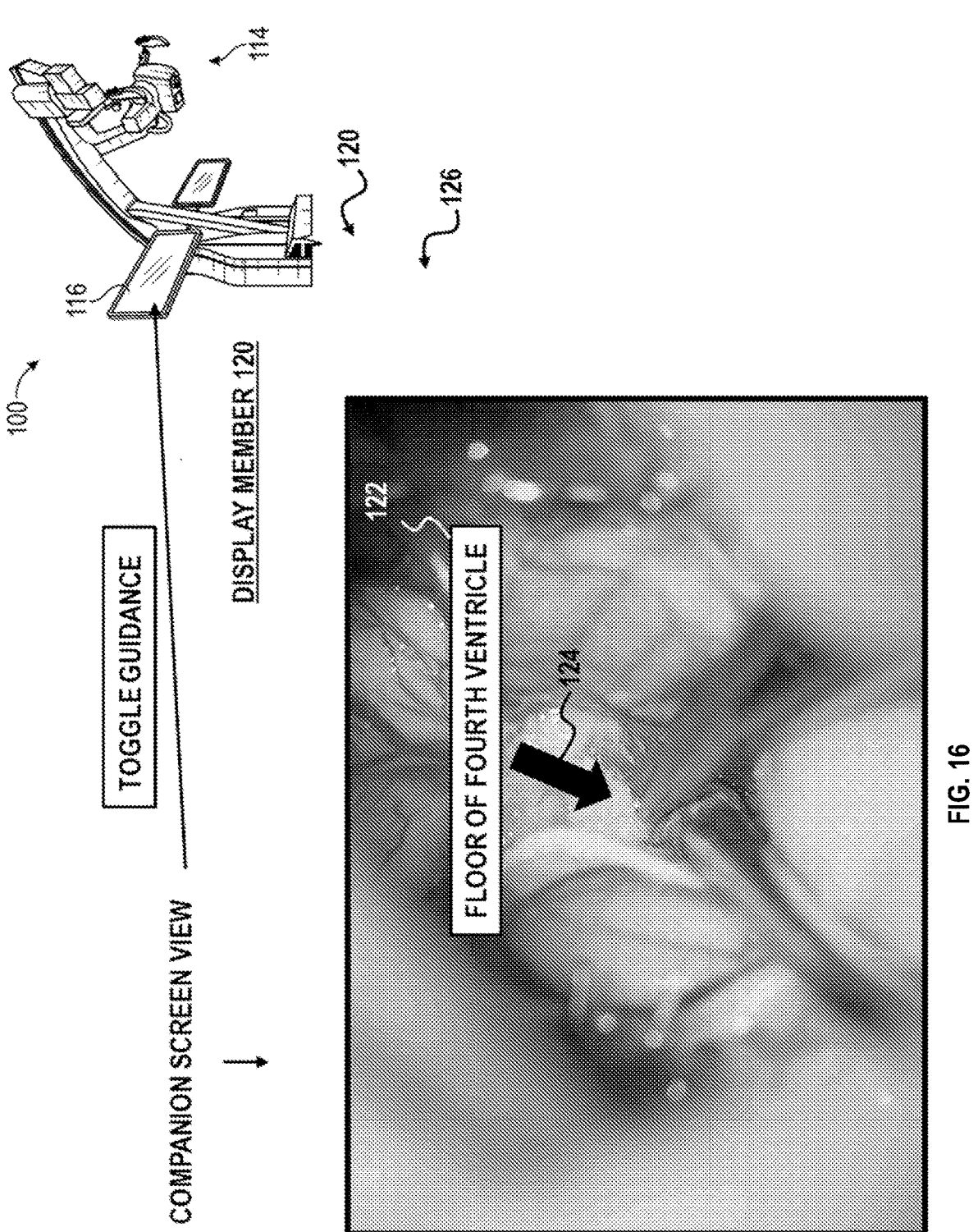
Figure 19:
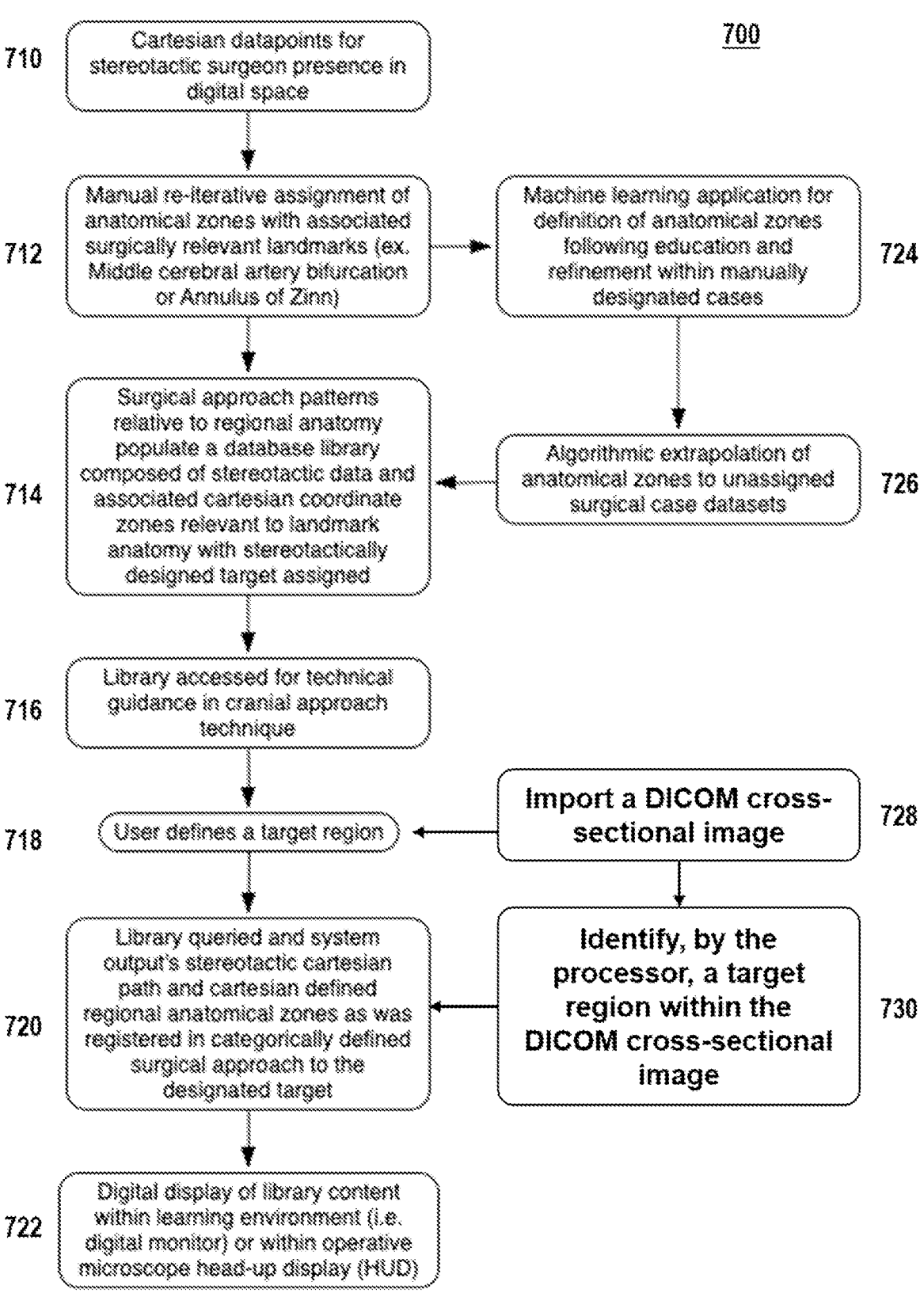
FIG. 19 is a process flow illustrating a process for populating and accessing approach library content from the system of FIG. 2.
Figure 20:
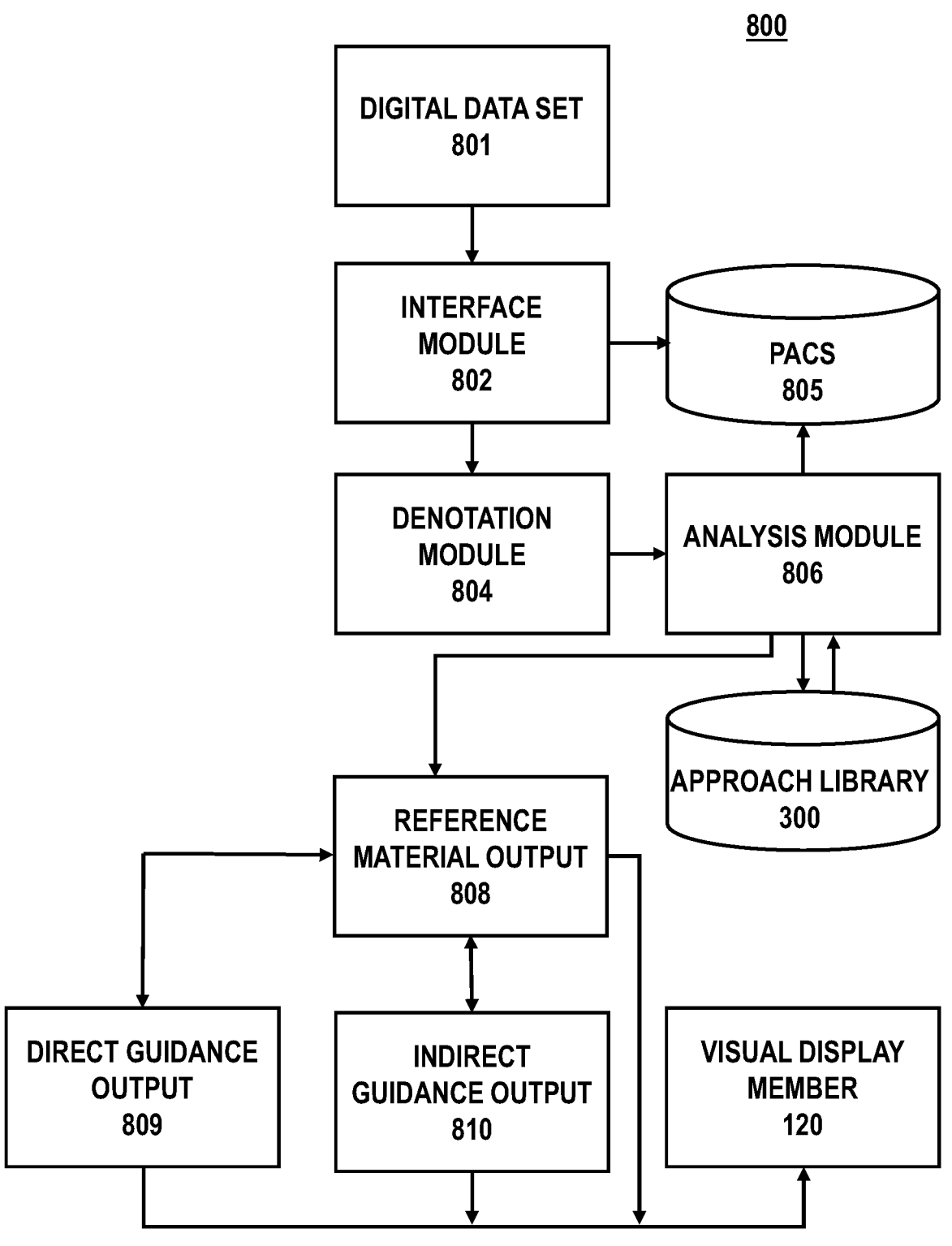
FIG. 20 is a simplified diagram showing an implementation of components of an Operating Microscope Guidance application of the system of FIG. 2.
Figure 21:
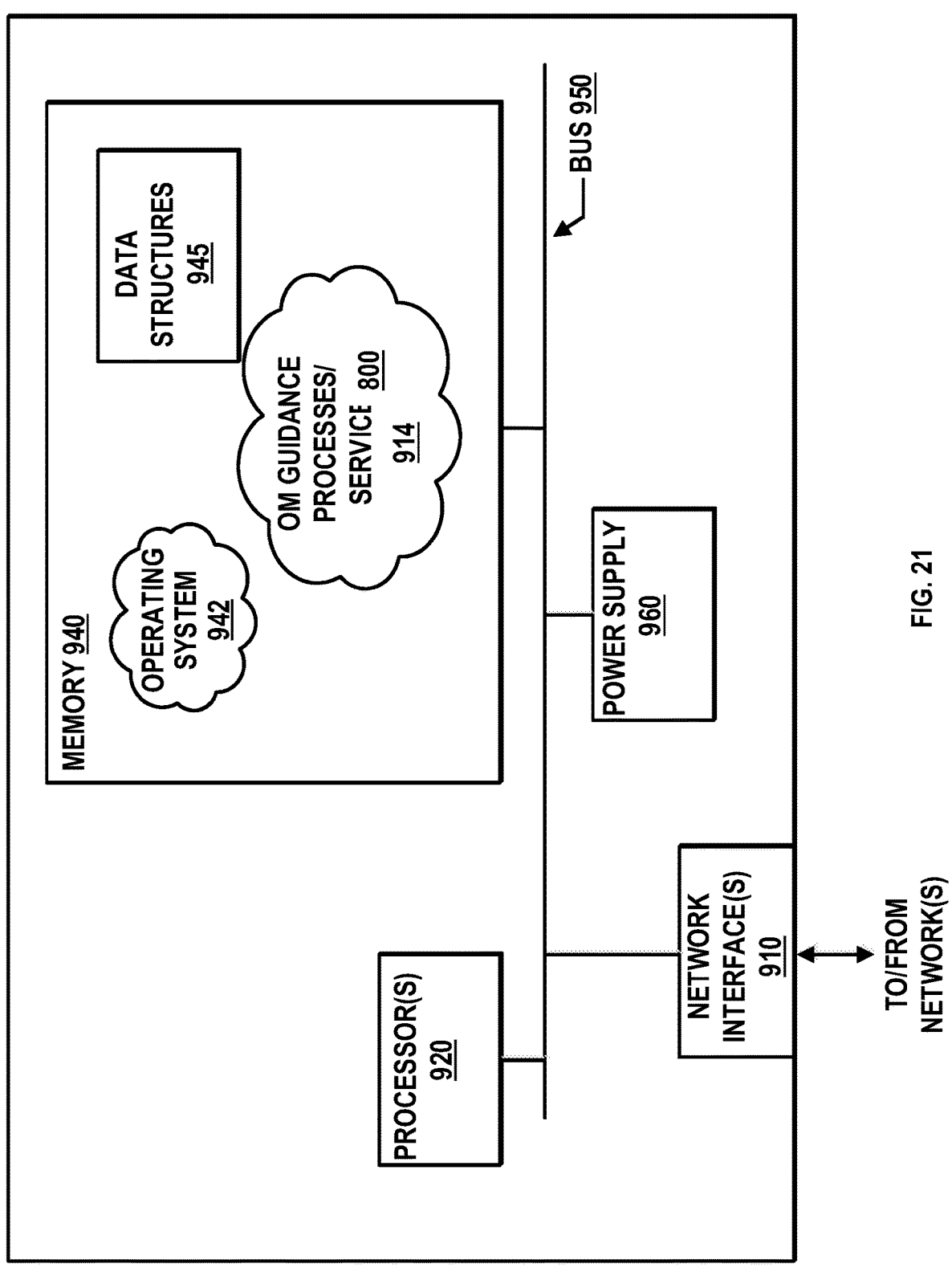
FIG. 21 is a simplified diagram showing an exemplary computing system for implementation of the system of FIG. 2.

In continued reference to FIGS. 2, 3, 5-7 and 11-16, the system 100 is further operable for providing direct intraoperative guidance based on the selected approach sequence 270. During a surgical case, the system 100 communicates with the OM 110 to extract the field of view 126 of the OM 110 in addition to recording Cartesian positional coordinates of the operating microscope to fill in the resultant approach log 230 of the plurality of approach logs 340 for the surgical case. The system 100 displays, by the display member 120, a video image including the field-of-view 126 captured by the OM 110 on the display member 120. In some embodiments, as shown in FIGS. 15 and 16, the display member 120 is a heads-up-display within of the OM 110 or an external display in communication with the OM 110.

During the surgical case, the system 100 iteratively determines a real-time Cartesian position of a focal point 222 of the OM 110 relative to the stereotactic Cartesian coordinate system defined with respect to patient anatomy. In some embodiments, this is achieved by first receiving the real-time Cartesian position of the hind point 214 of the OM 110 and the known focal length 216 of the OM 110. The system 100 can then determine a real-time Cartesian position of a focal point 222 of the OM 110 based on the real-time Cartesian position of the hind point 214 and the known focal length 216 of the OM 110.

Based on the real-time position of the focal point 222 of the OM 110, the system 100 displays, by the display member 120, a landmark identifier 122 at the estimated Cartesian zone 396 of a landmark region 380 within the field of view 126 captured by the OM 110 based on the real-time cartesian position of the focal point of the OM 110. The estimated Cartesian zone 396 of the landmark region 380 corresponds to an estimated position of the landmark region 380 based on one or more recorded landmark positions 394 associated with the landmark region 380 within the stereotactic Cartesian coordinate system. The system 100 displays the landmark identifier 122 when the Cartesian position of the focal point 222 of the OM 110 is approximately equal to the estimated Cartesian zone 396 of the landmark region 380 as dictated by the approach library 300. The system 100 further displays a landmark identifier 122 and a directional identifier 124 indicating a direction leading to an estimated Cartesian zone 396 of a future landmark region 380 associated with a future step of the plurality of steps of the selected approach sequence 430 relative to the real-time cartesian position of the focal point 222 of the OM 110. This is repeated iteratively until the focal point 222 of the OM 110 reaches the target region 410.

Referring to FIG. 17, a process flow 500 is illustrated showing a method for providing intra-operative guidance to a practitioner by the system 100. At block 510, prior to operation, the processor 920 of the system 100 defines a stereotactic cartesian coordinate system with respect to patient anatomy using imaging data 10 acquired through cross-sectional imaging. At block 520, the processor 920 receives a target region 250 and a starting position 260 with respect to patient anatomy. At block 530, the processor 920 selects a selected approach sequence 270 from the approach library 300, wherein the selected approach sequence 270 dictates a plurality of selected landmark regions 272 associated with a plurality of steps along a sequential path between the starting position 260 and the target region 250, wherein each selected landmark region 272 of the plurality of landmark regions 380 is associated with an estimated cartesian zone 396 defined within the approach library 300. At block 540, the processor 920 iteratively determines a real-time cartesian position of a focal point of an operative microscope 110 relative to the stereotactic cartesian coordinate system during a surgical case. At block 550, the processor 920 displays, by the display member 120, a landmark identifier 122 at the estimated cartesian zone of a landmark region 380 within a field of view 126 captured by the operating microscope 110 based on the real-time cartesian position of the focal point of the operating microscope 110. At block 560, the processor 920 displays, by the display member 120, a directional identifier 124 indicating a direction leading to an estimated Cartesian zone 396 of a future landmark region 380 associated with a future step of the plurality of steps of the selected approach sequence 270 relative to the real-time Cartesian position of the focal point of the operating microscope 110. As the focal point of the operating microscope 110 progresses along the selected approach sequence 270, blocks 540, 550 and 560 are iteratively repeated until the focal point reaches the target region 250.

Referring to FIG. 18, a process flow 700 is illustrated showing a method for populating the approach library 300 and displaying approach library content by the system 100. At block 710, the system 100 collects Cartesian data points 220 to populate an approach log 340 to characterize surgeon presence in a digital space. At block 712, the system 100 enables manual re-iterative assignment of Cartesian anatomical zones to one or more landmark regions 380 (anatomical zones). In some embodiments, as shown in blocks 724 and 725, the system 100 can utilize one or more machine-learning techniques in order to automatically assign Cartesian anatomical zones to one or more landmark regions 380. As shown in blocks 714, the system 100 populates the approach library 300 with an approach sequence 320 described by the approach log 340 along with approach sequence data 330 and relevant landmark region data 390. At block 716, the system 100 accesses the approach library 300 for technical guidance for a surgical case. At block 718, the system 100 receives a target region 410 as input to search the approach library 300 for one or more approach sequence options 430. In some embodiments, at block 728, the system 100 imports a DICOM cross-sectional image such as image data 10. At block 730, the system 100 identifies a target region 410 within the DICOM cross-sectional image. At block 720, the system 100 provides one or more approach sequence options 430 and associated approach sequence data 330 based on the target region 410. At block 722, the system 100 displays selected content from the approach library 300 on a display member 120.

In some embodiments an application 800 of the system 100 for the optimization of surgical approaches to cranial lesions such as, for example, malignant and/or benign cancerous tissue, vascular lesion, and/or infected tissue, can be implemented by a practitioner by obtaining digital data 801 in the form of cross-sectional imaging data of a patient's lesion pathology and inputting it into the application 800 wherein the obtained digital data 801 presents lesional pathology of the patient localizable to cartesian coordinates or a cartesian volume. The application 800 can include component software programs including: an interface module 802, a denotation module 804, and an analysis module 806. The interface module 802 and/or the analysis module 806 can access a Picture Archiving and Communications System (PACS) 805 and/or the approach library 300 for the purpose of comparison with inputted digital data 801. Interface with the software and software outputs can be displayed to a practitioner via a visual display member 120. Upon inputting digital data 801 presenting the patient's lesion pathology, a practitioner can indicate via the interface module 802, within the denotation module 804, the patient's lesion cartesian coordinate(s) or cartesian volume. The analysis module 806 can then programmatically compare Cartesian coordinate(s) or cartesian volume of the indicated lesion to the target cartesian coordinate(s) or cartesian volume presented within the datasets of the approach library 300. In some embodiments, the approach library can additionally include one or more or digital data sets pre-populated with lesion pathology for the purpose of comparison to inputted surgical stereotactic tracking datasets within the approach library 300, comprising a plurality of stereotactic surgical datasets with defined cartesian target coordinate(s) or cartesian volumes retrievable by the analysis module 806 during such a comparison. Past inputted digital data 801 archived within the PACS 205 can also be compared to presently inputted digital data sets 801. Stereotactic surgical dataset targets programmatically determined generally or substantially similar to aspects of surgical target indicated in inputted digital data sets 801 can be presented to the practitioner via the visual display member 120, and can be accompanied by an instructional reference material output

808 to aid the practitioner in their preparation and performance of a surgical approach to treat the lesion. The reference material output 808 can include a plurality of resources having direct guidance outputs 809 comprising graphic representations superimposed upon the inputted cross-sectional images, within the graphical representation of the operating room microscopes perspective, or within the HUD of the operating microscope for viewing by the surgeon, and indirect guidance outputs 810. The indirect guidance outputs 810 include stereotactic target specific internet links to scholarly publications, video demonstrations, and/or an online system-enabled discussion of aspects of recommended approaches. PACS 805 can be implemented by the interface module 802 and/or the analysis module 806 wherein inputted digital data 801 can be stored for later queried retrieval and/or comparison.

In some embodiments, a plurality of target cartesian coordinate(s) or cartesian volume(s) can be present in a single patient and digital data 801 taken of the patient's pathology wherein the practitioner can obtain digital data 801 presenting the patient's lesion pathology via a plurality of imaging methods, for example computerized tomography, magnetic resonance imaging, and other imaging methods are contemplated as a manner of collecting digital data 801. In such cases when digital data 801 are obtained from imaging devices, digital data 801 can comprise digital images. In these cases, digital data 801 obtained from imaging device (s), such as a CT scanner or MRI device for example, can be inputted directly into the interface module 802. In some cases, however, digital data 801 presenting the patient's lesion pathology may have already been obtained, as in cases such as patients requiring transference to different hospitals, where digital data 801 have been obtained at a hospital prior to the patient's transference. In cases where digital data 801 have already been obtained, instead of a practitioner obtaining the digital data 801 from an imaging device, the practitioner can retrieve the digital data 801 via a plurality of methods, for example via remote computer, removable memory device, and/or from the PACS 805, and can input the retrieved digital data 801 into the interface module 802 by any manner which the method of retrieval accommodates.

In some embodiments lesion pathology can be indicated by the practitioner by accessing the interface module 802 to outline the cartesian coordinate(s) or cartesian volume(s) of the cranial approach target presented by the inputted digital data in three coordinate planes via a denotation module 804 comprising a free-hand software tool.

In some embodiments lesion pathology can be indicated by the practitioner by accessing the interface module 802 to outline the cartesian coordinate(s) or cartesian volume(s) of the surgical approach target presented by the inputted digital data in three coordinate planes via a denotation module 804 comprising a programmatically generated menu of stencils to overlay, size to fit, and/or outline a lesion pathology in three coordinate planes.

In some embodiments lesion pathology can be indicated by the practitioner by accessing the interface module 802 to select from the denotation module 804 a surgical approach target presented by the inputted digital data describing the cartesian coordinate(s) or cartesian volume(s) from a programmatically generated menu of anticipated or programmatically computed cartesian coordinate(s) or cartesian volume(s).

In some embodiments, where a sufficient amount of digital data 801 cannot be obtained and/or inputted to indicate the surgical approach target in cartesian coordinate (s) or cartesian volume(s), a lesser number of digital data 801 presenting lesion pathology in two dimensions can be inputted into the interface module 802.

In some embodiments the indicated lesion pathology presented by inputted digital data can be programmatically compared and/or analyzed via the analysis module 806 to individual stereotactic surgical datasets 807 via any combination of measurements from the non-exhaustive examples of: depths, densities, spatial positional locations, and/or geometric measurements (such as circumference, surface area, and volume, for example, while additional measurements are contemplated) of cartesian coordinate(s) or cartesian volume(s) associated with the surgical approach target.

In some embodiments the indicated surgical approach target can be manually compared and/or analyzed to individual stereotactic surgical datasets within the approach library 300 by an interfacing practitioner wherein the interfacing practitioner can access the approach library 300 to select individual, or averaged surgical approach datasets with surgical approach target(s) believed by the practitioner to be most applicable the library patient's surgical approach target by inputted digital data.

In summary, the disclosed system 100 enables a surgeon recording platform permissive of acquiring datasets that includes a position, focal length, and thereby focal point of an operating microscope relative to the patient's surgical anatomy. This system therefore possesses multiple educational, analytical, efficiency, quality improvement, and clinical outcome altering applications.

Computer-Implemented System

FIG. 10 is a schematic block diagram of an example device 900 that may be used with one or more embodiments described herein, e.g., as a component of system 100 shown in FIG. 2.

Device 900 comprises one or more network interfaces 910 (e.g., wired, wireless, PLC, etc.), at least one processor 920, and a memory 940 interconnected by a system bus 950, as well as a power supply 960 (e.g., battery, plug-in, etc.).

Network interface(s) 910 include the mechanical, electrical, and signaling circuitry for communicating data over the communication links coupled to a communication network. Network interfaces 910 are configured to transmit and/or receive data using a variety of different communication protocols. As illustrated, the box representing network interfaces 910 is shown for simplicity, and it is appreciated that such interfaces may represent different types of network connections such as wireless and wired (physical) connections. Network interfaces 910 are shown separately from power supply 960, however it is appreciated that the interfaces that support PLC protocols may communicate through power supply 960 and/or may be an integral component coupled to power supply 960.

Memory 940 includes a plurality of storage locations that are addressable by processor 920 and network interfaces 910 for storing software programs and data structures associated with the embodiments described herein. In some embodiments, device 900 may have limited memory or no memory (e.g., no memory for storage other than for programs/processes operating on the device and associated caches).

Processor 920 comprises hardware elements or logic adapted to execute the software programs (e.g., instructions) and manipulate data structures 945. An operating system 942, portions of which are typically resident in memory 940 and executed by the processor, functionally organizes device 900 by, inter alia, invoking operations in support of software processes and/or services executing on the device. These software processes and/or services may include OM Guidance processes/services 800 described herein. Note that while OM Guidance network processes/services 800 is illustrated in centralized memory 940, alternative embodiments provide for the process to be operated within the network interfaces 910, such as a component of a MAC layer, and/or as part of a distributed computing network environment.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules or engines configured to operate in accordance with the techniques herein (e.g., according to the functionality of a similar process). In this context, the term module and engine may be interchangeable. In general, the term module or engine refers to model or an organization of interrelated software components/functions. Further, while the OM Guidance network processes/services 800 is shown as a standalone process, those skilled in the art will appreciate that this process may be executed as a routine or module within other processes.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system, comprising:
a computer-implemented system including a processor in communication with a display member and a memory, the memory including instructions, which, when executed, cause the processor to:
define a stereotactic Cartesian coordinate system with respect to patient anatomy using imaging data acquired through cross-sectional imaging;
receive a target region and a starting position with respect to patient anatomy;
select an approach sequence from an approach library, wherein the approach sequence dictates a plurality of landmark regions associated with a plurality of steps along a sequential path between the starting position and the target region, wherein each landmark region of the plurality of landmark regions is associated with an estimated Cartesian zone defined within the approach library;
iteratively determine a real-time Cartesian position of a focal point of an operative microscope relative to the stereotactic Cartesian coordinate system;
display, by the display member, a landmark identifier at the estimated Cartesian zone of a landmark region within a field of view captured by the operative microscope based on the real-time Cartesian position of the focal point of the operative microscope; and
display, by the display member, a directional identifier indicating a direction leading to an estimated Cartesian zone of a future landmark region associated with a future step of the plurality of steps of the approach sequence relative to the real-time Cartesian position of the focal point of the operative microscope,
wherein the approach library includes:
a landmark index including landmark region data associated with a plurality of landmark regions, wherein the landmark region data for a landmark region of the plurality of landmark regions includes:
a plurality of recorded landmark positions within the stereotactic Cartesian coordinate system; and
the estimated Cartesian zone associated with the landmark region, wherein the estimated Cartesian zone is representative of a three-dimensional region within the stereotactic Cartesian coordinate system based on the plurality of recorded landmark positions.

2. The system of claim 1, wherein the memory further includes instructions, which, when executed, further cause the processor to:
associate the target region and the starting position with a respective Cartesian coordinate value with respect to the stereotactic Cartesian coordinate system.

3. The system of claim 1, wherein the approach library includes:
an approach sequence index including a plurality of approach sequences, wherein the plurality of approach sequences is categorically organized within the approach sequence index.

4. The system of claim 1, wherein one or more recorded landmark positions of the plurality of recorded landmark positions are associated with a respective Cartesian datapoint instance denoting a Cartesian position of a focal point of an operative microscope at a time step during a surgical case.

5. The system of claim 1, wherein one or more recorded landmark positions of the plurality of recorded landmark positions are associated with a recorded Cartesian location of a landmark region obtained using cross-sectional imaging.

6. The system of claim 1, wherein the approach library includes:
a set of Cartesian datapoints including a plurality of Cartesian datapoint instances associated with a Cartesian position of a focal point of an operative microscope recorded throughout a previously-recorded surgical case of a plurality of previously-recorded surgical cases, wherein the set of Cartesian datapoints is recorded at each time step of a plurality of time steps throughout the previously-recorded surgical case.

7. The system of claim 1, wherein the memory further includes instructions, which, when executed, further cause the processor to:
associate a landmark region with a respective Cartesian zone of the stereotactic Cartesian coordinate system.

8. The system of claim 7, wherein the Cartesian zone of the landmark region corresponds to an estimated position of the landmark region based on one or more recorded landmark positions within the stereotactic Cartesian coordinate system.

9. The system of claim 1, wherein the memory further includes instructions, which, when executed, further cause the processor to:
associate each step of the approach sequence with a respective landmark region.

10. The system of claim 1, wherein the memory further includes instructions, which, when executed, further cause the processor to:
display, by the display member, a video image including the field-of-view captured by the operative microscope on a display member.

11. The system of claim 10, wherein the display member is a heads-up-display of the operative microscope or an external display in communication with the operative microscope.

12. The system of claim 1, wherein the memory further includes instructions, which, when executed, further cause the processor to:

receive a real-time Cartesian position of the operative microscope relative to the stereotactic Cartesian coordinate system.

13. The system of claim 12, wherein the memory further includes instructions, which, when executed, further cause the processor to:

determine a real-time Cartesian position of a focal point of the operative microscope based on the real-time Cartesian position of the operative microscope.

14. The system of claim 1, wherein the memory further includes instructions, which, when executed, further cause the processor to:

query the approach library to identify an approach sequence of a plurality of approach sequences indicative of the sequential path between the starting position and the target region.

15. The system of claim 1, wherein the memory further includes instructions, which, when executed, further cause the processor to:

provide one or more starting positions associated with a target region based on one or more approach sequences associated with the target region.

16. The system of claim 1, wherein the memory further includes instructions, which, when executed, further cause the processor to:

display a landmark identifier associated with the future landmark region associated with the future step of the plurality of steps of the approach sequence.

17. The system of claim 1, wherein the landmark identifier associated with the landmark region is displayed when the real-time Cartesian position of the focal point of an operative microscope lies within estimated Cartesian zone of the landmark region as dictated by the approach library.

18. The system of claim 1, wherein the memory further includes instructions, which, when executed, further cause the processor to:

align the operative microscope with a previously-recorded focal point and hind point combination associated with a landmark region.

19. The system of claim 1, wherein the memory further includes instructions, which, when executed, cause the processor to:

receive a selection of a landmark region from the plurality of landmark regions within the approach library; and display, by the display member, a directional indicator or laser guidance indicator to indicate a direction towards an estimated Cartesian zone associated with the landmark region.

20. A system comprising:

a computer-implemented system including a processor in communication with a display member and a memory, the memory including instructions, which, when executed, cause the processor to:

define a stereotactic Cartesian coordinate system with respect to patient anatomy using imaging data acquired through cross-sectional imaging;

receive a target region and a starting position with respect to patient anatomy;

select an approach sequence from an approach library, wherein the approach sequence dictates a plurality of landmark regions associated with a plurality of steps along a sequential path between the starting position and the target region, wherein each landmark region of the plurality of landmark regions is associated with an estimated Cartesian zone defined within the approach library;

iteratively determine a real-time Cartesian position of a focal point of an operative microscope relative to the stereotactic Cartesian coordinate system;

display, by the display member, a landmark identifier at the estimated Cartesian zone of a landmark region within a field of view captured by the operative microscope based on the real-time Cartesian position of the focal point of the operative microscope; and display, by the display member, a directional identifier indicating a direction leading to an estimated Cartesian zone of a future landmark region associated with a future step of the plurality of steps of the approach sequence relative to the real-time Cartesian position of the focal point of the operative microscope, wherein the landmark identifier associated with the landmark region is displayed when the real-time Cartesian position of the focal point of the operative microscope lies within the estimated Cartesian zone of the landmark region as dictated by the approach library.

* * * * *